United States Patent
Rabiner et al.

(10) Patent No.: US 8,906,030 B2
(45) Date of Patent: *Dec. 9, 2014

(54) SYSTEMS AND METHODS FOR INTERNAL BONE FIXATION

(75) Inventors: Robert A. Rabiner, Tiverton, RI (US); Dennis P. Colleran, North Attleboro, MA (US); Anthony W. O'Leary, Walpole, MA (US); Justin G. Dye, Mansfield, MA (US); Mark A. Drew, Barrington, RI (US)

(73) Assignee: IlluminOss Medical, Inc., East Providence, RI (US)

( * ) Notice: Subject to any disclaimer, the term of this patent is extended or adjusted under 35 U.S.C. 154(b) by 285 days.

This patent is subject to a terminal disclaimer.

(21) Appl. No.: 13/616,781

(22) Filed: Sep. 14, 2012

(65) Prior Publication Data

US 2013/0066326 A1      Mar. 14, 2013

Related U.S. Application Data

(63) Continuation of application No. 12/983,496, filed on Jan. 3, 2011, now Pat. No. 8,734,460, which is a (Continued)

(51) Int. Cl.
*A61B 17/88* (2006.01)
(Continued)

(52) U.S. Cl.
CPC .............. *A61B 17/8816* (2013.01); *A61B 17/68* (2013.01); *A61B 17/7097* (2013.01);
(Continued)

(58) Field of Classification Search
CPC ........... A61B 17/7097; A61B 17/7275; A61B 17/7091; A61B 17/8816; A61B 17/8836; A61B 17/68; A61B 17/8819; A61B 2017/00557; A61B 2019/5206; A61B 17/8833
USPC ..................... 606/62–68, 92–94; 604/21, 508
See application file for complete search history.

(56) References Cited

U.S. PATENT DOCUMENTS

| 4,280,233 A | 7/1981 | Raab |
| 4,294,251 A | 10/1981 | Greenwald et al. |

(Continued)

FOREIGN PATENT DOCUMENTS

| DE | 40 28 466 | 3/1992 |
| EP | 0 709 698 | 5/1996 |

(Continued)

OTHER PUBLICATIONS

USPTO Office Action in U.S. Appl. No. 12/859,680 mailed Nov. 9, 2012.

(Continued)

*Primary Examiner* — Pedro Philogene
(74) *Attorney, Agent, or Firm* — Greenberg Traurig, LLP; David J. Dykeman; Danielle T. Abramson

(57) ABSTRACT

Internal bone fixation devices and methods for using the devices for repairing a weakened or fractured bone are disclosed herein. In an aspect, a device for repairing a fractured bone includes a delivery catheter having an elongated shaft with a proximal end, a distal end, and a longitudinal axis therebetween, the delivery catheter having an inner void for passing at least one reinforcing material, and an inner lumen for accepting a light pipe, wherein a distal end of the inner lumen terminates in an optical lens; a conformable member releasably engaging the distal end of the delivery catheter, the conformable member moving from a deflated state to an inflated state when the at least one reinforcing material is delivered to the conformable member; and an adapter releasably engaging the proximal end of the delivery catheter for receiving the light pipe and the at least one reinforcing material.

20 Claims, 17 Drawing Sheets

Related U.S. Application Data continuation of application No. 12/262,411, filed on Oct. 31, 2008, now Pat. No. 7,879,041, which is a continuation-in-part of application No. 11/903,123, filed on Sep. 20, 2007, now Pat. No. 7,811,284.

(60) Provisional application No. 60/858,202, filed on Nov. 10, 2006, provisional application No. 60/880,646, filed on Jan. 16, 2007.

(51) Int. Cl.
    *A61B 17/68* (2006.01)
    *A61B 17/70* (2006.01)
    *A61B 17/72* (2006.01)
    *A61B 17/00* (2006.01)
    *A61B 19/00* (2006.01)

(52) U.S. Cl.
    CPC .......... *A61B 17/7275* (2013.01); *A61B 17/7291* (2013.01); *A61B 17/8836* (2013.01); *A61B 17/8819* (2013.01); *A61B 17/8833* (2013.01); *A61B 2017/00557* (2013.01); *A61B 2019/5206* (2013.01)
    USPC .......................................................... 606/93

(56) References Cited

U.S. PATENT DOCUMENTS

| | | | |
|---|---|---|---|
| 4,313,434 | A | 2/1982 | Segal |
| 4,341,691 | A | 7/1982 | Anuta |
| 4,369,772 | A | 1/1983 | Miller |
| 4,414,608 | A | 11/1983 | Furihata |
| 4,422,719 | A | 12/1983 | Orcutt |
| 4,433,898 | A | 2/1984 | Nasiri |
| 4,462,394 | A | 7/1984 | Jacobs |
| 4,466,435 | A | 8/1984 | Murray |
| 4,562,598 | A | 1/1986 | Kranz |
| 4,686,973 | A | 8/1987 | Frisch |
| 4,697,584 | A | 10/1987 | Haynes |
| 4,735,625 | A | 4/1988 | Davidson |
| 4,870,953 | A | 10/1989 | DonMichael et al. |
| 4,888,024 | A | 12/1989 | Powlan |
| 4,904,391 | A | 2/1990 | Freeman |
| 4,961,424 | A | 10/1990 | Kubota et al. |
| 4,963,151 | A | 10/1990 | Ducheyne et al. |
| 4,969,888 | A | 11/1990 | Scholten et al. |
| 5,030,093 | A | 7/1991 | Mitnick |
| 5,049,157 | A | 9/1991 | Mittelmeier et al. |
| 5,085,660 | A | 2/1992 | Lin |
| 5,092,899 | A | 3/1992 | Forte |
| 5,102,413 | A | 4/1992 | Poddar |
| 5,108,404 | A | 4/1992 | Scholten et al. |
| 5,112,333 | A | 5/1992 | Fixel |
| 5,207,669 | A * | 5/1993 | Baker et al. ................ 606/7 |
| 5,295,733 | A | 3/1994 | LeBegue |
| 5,295,962 | A | 3/1994 | Crocker et al. |
| 5,303,718 | A | 4/1994 | Krajicek |
| 5,316,550 | A | 5/1994 | Forte |
| 5,336,699 | A | 8/1994 | Cooke et al. |
| 5,372,598 | A | 12/1994 | Luhr et al. |
| 5,391,144 | A | 2/1995 | Sakurai et al. |
| 5,415,654 | A | 5/1995 | Daikuzono |
| 5,423,850 | A | 6/1995 | Berger |
| 5,432,876 | A | 7/1995 | Appeldorn et al. |
| 5,443,468 | A | 8/1995 | Johnson |
| 5,462,552 | A | 10/1995 | Kiester |
| 5,480,400 | A | 1/1996 | Berger |
| 5,538,514 | A | 7/1996 | Hawkins |
| 5,548,676 | A | 8/1996 | Savage, Jr. |
| 5,554,111 | A | 9/1996 | Morrey et al. |
| 5,556,429 | A | 9/1996 | Felt |
| 5,571,204 | A | 11/1996 | Nies |
| 5,658,310 | A | 8/1997 | Berger |
| 5,658,963 | A | 8/1997 | Qian et al. |
| 5,705,181 | A | 1/1998 | Cooper et al. |
| 5,707,374 | A | 1/1998 | Schmidt |
| 5,713,901 | A | 2/1998 | Tock |
| 5,795,353 | A | 8/1998 | Felt |
| 5,824,087 | A | 10/1998 | Aspden et al. |
| 5,827,289 | A | 10/1998 | Reiley et al. |
| 5,888,220 | A | 3/1999 | Felt et al. |
| 5,897,557 | A | 4/1999 | Chin et al. |
| 5,908,433 | A | 6/1999 | Eager et al. |
| 5,972,015 | A | 10/1999 | Scribner et al. |
| 5,980,075 | A | 11/1999 | Sheaffer |
| 5,980,253 | A | 11/1999 | Oxman et al. |
| 5,987,199 | A | 11/1999 | Zarian et al. |
| 5,989,230 | A | 11/1999 | Frassica |
| 6,008,264 | A | 12/1999 | Ostler |
| 6,019,761 | A | 2/2000 | Gustilo |
| 6,019,774 | A | 2/2000 | Weiss et al. |
| 6,033,411 | A | 3/2000 | Preissman |
| 6,039,762 | A | 3/2000 | McKay |
| 6,042,380 | A | 3/2000 | De Rowe |
| 6,048,346 | A | 4/2000 | Reiley et al. |
| 6,059,789 | A | 5/2000 | Dinger et al. |
| 6,066,154 | A | 5/2000 | Reiley et al. |
| 6,079,868 | A | 6/2000 | Rydell |
| 6,103,203 | A | 8/2000 | Fischer |
| 6,110,176 | A | 8/2000 | Shapira |
| 6,121,341 | A | 9/2000 | Sawhney et al. |
| 6,127,597 | A | 10/2000 | Beyar et al. |
| 6,140,452 | A | 10/2000 | Felt et al. |
| 6,159,236 | A * | 12/2000 | Biel ........................... 607/92 |
| 6,179,852 | B1 | 1/2001 | Strickland et al. |
| 6,195,477 | B1 | 2/2001 | Denuto et al. |
| 6,200,134 | B1 | 3/2001 | Kovac et al. |
| 6,217,581 | B1 | 4/2001 | Tolson |
| 6,223,085 | B1 | 4/2001 | Dann et al. |
| 6,224,630 | B1 | 5/2001 | Bao et al. |
| 6,235,043 | B1 | 5/2001 | Reiley et al. |
| 6,241,734 | B1 | 6/2001 | Scribner et al. |
| 6,248,110 | B1 | 6/2001 | Reiley et al. |
| 6,248,131 | B1 | 6/2001 | Felt et al. |
| 6,258,089 | B1 | 7/2001 | Campbell et al. |
| 6,261,289 | B1 | 7/2001 | Levy |
| 6,280,456 | B1 | 8/2001 | Scribner et al. |
| 6,282,013 | B1 | 8/2001 | Ostler et al. |
| 6,290,382 | B1 | 9/2001 | Bourn et al. |
| 6,299,597 | B1 | 10/2001 | Buscemi et al. |
| 6,306,177 | B1 | 10/2001 | Felt et al. |
| 6,319,255 | B1 | 11/2001 | Grundei et al. |
| 6,332,894 | B1 | 12/2001 | Stalcup et al. |
| 6,336,914 | B1 | 1/2002 | Gillespie, III |
| 6,336,930 | B1 | 1/2002 | Stalcup et al. |
| 6,358,252 | B1 | 3/2002 | Shapira |
| 6,387,098 | B1 | 5/2002 | Cole et al. |
| 6,395,007 | B1 | 5/2002 | Bhatnagar et al. |
| 6,416,531 | B2 | 7/2002 | Chen |
| 6,416,737 | B1 | 7/2002 | Manolagas et al. |
| 6,419,483 | B1 | 7/2002 | Adam et al. |
| 6,423,083 | B2 | 7/2002 | Reiley et al. |
| 6,425,923 | B1 | 7/2002 | Stalcup et al. |
| 6,440,444 | B2 | 8/2002 | Boyce et al. |
| 6,443,988 | B2 | 9/2002 | Felt et al. |
| 6,447,514 | B1 | 9/2002 | Stalcup et al. |
| 6,458,375 | B1 | 10/2002 | Gertzman et al. |
| 6,478,751 | B1 | 11/2002 | Krueger et al. |
| 6,485,512 | B1 | 11/2002 | Cheng |
| 6,494,883 | B1 | 12/2002 | Ferree |
| 6,524,251 | B2 | 2/2003 | Rabiner et al. |
| 6,524,313 | B1 | 2/2003 | Fassier et al. |
| 6,551,321 | B1 | 4/2003 | Burkinshaw et al. |
| 6,551,337 | B1 | 4/2003 | Rabiner et al. |
| 6,565,528 | B1 | 5/2003 | Mueller |
| 6,579,277 | B1 | 6/2003 | Rabiner et al. |
| 6,579,279 | B1 | 6/2003 | Rabiner et al. |
| 6,620,185 | B1 | 9/2003 | Harvie et al. |
| 6,623,505 | B2 | 9/2003 | Scribner et al. |
| 6,632,235 | B2 * | 10/2003 | Weikel et al. ................ 606/192 |
| 6,648,881 | B2 | 11/2003 | KenKnight et al. |
| 6,652,547 | B2 | 11/2003 | Rabiner et al. |
| 6,652,587 | B2 | 11/2003 | Felt et al. |

(56) References Cited

U.S. PATENT DOCUMENTS

| | | | |
|---|---|---|---|
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Rabiner et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 * | 2/2011 | Rabiner et al. ............... 606/93 |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim et al. |
| 8,210,729 B2 | 7/2012 | O'Leary et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 * | 2/2013 | Rabiner et al. ............... 606/63 |
| 8,403,968 B2 | 3/2013 | Rabiner et al. |
| 8,413,664 B2 | 4/2013 | Appling |
| 8,512,338 B2 | 8/2013 | Rabiner et al. |
| 8,574,233 B2 | 11/2013 | Rabiner et al. |
| 8,668,701 B2 * | 3/2014 | Rabiner ............... 606/94 |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,460 B2 * | 5/2014 | Rabiner et al. ............... 606/93 |
| 2001/0011174 A1 | 8/2001 | Reiley et al. |
| 2001/0044626 A1 | 11/2001 | Reiley et al. |
| 2002/0082600 A1 | 6/2002 | Shaolian et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 * | 8/2004 | Boucher et al. ............... 606/191 |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 * | 10/2005 | Shaolian et al. ............... 606/61 |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 * | 8/2006 | Ellman et al. ............... 606/93 |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |

(56) References Cited

U.S. PATENT DOCUMENTS

| | | |
|---|---|---|
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0118143 A1 * | 5/2007 | Ralph et al. ............ 606/92 |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0233146 A1 | 10/2007 | Henniges et al. |
| 2007/0255287 A1 | 11/2007 | Rabiner |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0082504 A1 | 4/2011 | Singhatt et al. |
| 2011/0098713 A1 | 4/2011 | Rabiner et al. |
| 2011/0110114 A1 | 5/2011 | Papac et al. |
| 2011/0118740 A1 | 5/2011 | Rabiner et al. |
| 2011/0160870 A1 | 6/2011 | Baumgartner et al. |
| 2011/0166306 A1 | 7/2011 | Stansbury et al. |
| 2011/0313356 A1 | 12/2011 | Rabiner et al. |
| 2012/0029102 A1 | 2/2012 | Rose et al. |
| 2012/0041557 A1 | 2/2012 | Frigg |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0158607 A1 | 6/2013 | Rabiner et al. |
| 2013/0184715 A1 | 7/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/039811 | 4/2008 |
| WO | WO 2008/063265 | 5/2008 |
| WO | WO 2009/059090 | 5/2009 |
| WO | WO 2009/064847 | 5/2009 |
| WO | WO 2009/082688 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO2013/059609 | 4/2013 |
| WO | WO 2014/100427 | 6/2014 |

OTHER PUBLICATIONS

USPTO Office Action in U.S. Appl. No. 12/943,544 mailed Dec. 3, 2012.

USPTO Office Action in U.S. Appl. No. 12/859,680 mailed Jan. 17, 2013.

USPTO Office Action in U.S. Appl. No. 12/262,370 mailed Dec. 14, 2012.

International Search Report and Written Opinion for PCT/US2012/061047 mailed Jan. 7, 2013.

(56) References Cited

OTHER PUBLICATIONS

USPTO Office Action in U.S. Appl. No. 12/756,014 mailed Jan. 22, 2013.
USPTO Office Action in U.S. Appl. No. 13/088,916 mailed Jan. 23, 2013.
Extended European Search Report based on EP 10 76 2390 dated Oct. 30, 2013.
USPTO Office Action in U.S. Appl. No. 12/262,370 mailed Nov. 21, 2013.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.
Jovanovic et al., "Fixion Nails for Humeral Fractures, Injury", Int. J. Care Injured, vol. 35, Issue 11, pp. 1140-1142, Nov. 2004.
Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
PCT International Search Report based on PCT/US07/20402 dated Apr. 1, 2008.
PCT International Search Report based on PCT/US07/10050 dated Apr. 17, 2008.
PCT International Search Report based on PCT/US07/10038 dated Aug. 27, 2008.
PCT International Search Report based on PCT/US08/81929 dated Jan. 12, 2009.
PCT International Search Report based on PCT/US08/81924 dated Feb. 9, 2009.
PCT International Search Report based on PCT/US08/87630 dated Feb. 24, 2009.
PCT International Search Report based on PCT/US10/30275 dated Aug. 11, 2010.
PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
PCT International Search Report based on PCT/US11/66871 dated May 1, 2012.
USPTO Office Action in U.S. Appl. No. 11/789,906 mailed Apr. 29, 2009.
USPTO Office Action in U.S. Appl. No. 11/789,906 mailed Mar. 11, 2010.
USPTO Office Action in U.S. Appl. No. 11/789,906 mailed Apr. 30, 2010.
USPTO Office Action in U.S. Appl. No. 11/789,907 mailed May 11, 2010.
USPTO Office Action in U.S. Appl. No. 11/903,123 mailed Jul. 1, 2010.
USPTO Office Action in U.S. Appl. No. 11/964,370 mailed Dec. 9, 2010.
USPTO Office Action in U.S. Appl. No. 11/964,370 mailed Apr. 28, 2011.
USPTO Office Action in U.S. Appl. No. 11/964,370 mailed Sep. 23, 2011.
USPTO Office Action in U.S. Appl. No. 11/964,370 mailed Mar. 16, 2012.
USPTO Office Action in U.S. Appl. No. 12/262,411 mailed Sep. 1, 2010.
USPTO Office Action in U.S. Appl. No. 12/755,784 mailed Dec. 23, 2011.
USPTO Office Action in U.S. Appl. No. 12/756,014 mailed May 11, 2012.
USPTO Office Action in U.S. Appl. No. 12/858,924 mailed Oct. 24, 2011.
USPTO Office Action in U.S. Appl. No. 12/858,924 mailed Apr. 4, 2012.
USPTO Office Action in U.S. Appl. No. 12/875,460 mailed Mar. 8, 2012.
USPTO Office Action in U.S. Appl. No. 12/886,288 mailed Dec. 27, 2011.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 13/772,947 mailed Jun. 19, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
USPTO Office Action in U.S. Appl. No. 13/617,557 mailed Oct. 9, 2013.
USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
USPTO Office Action in U.S. Appl. No. 13/553,247 mailed May 7, 2014.
Extended European Search Report based on EP 14156473 dated May 13, 2014.

(56) References Cited

OTHER PUBLICATIONS

USPTO Office Action in U.S. Appl. No. 13/800,518 mailed Jun. 10, 2014.
USPTO Office Action in U.S. Appl. No. 12/262,370 mailed Jun. 26, 2014.
USPTO Office Action in U.S. Appl. No. 13/617,557 mailed Jun. 27, 2014.
USPTO Office Action in U.S. Appl. No. 13/335,110 mailed Jul. 31, 2014.
USPTO Office Action in U.S. Appl. No. 13/730,521 mailed Sep. 8, 2014.

* cited by examiner

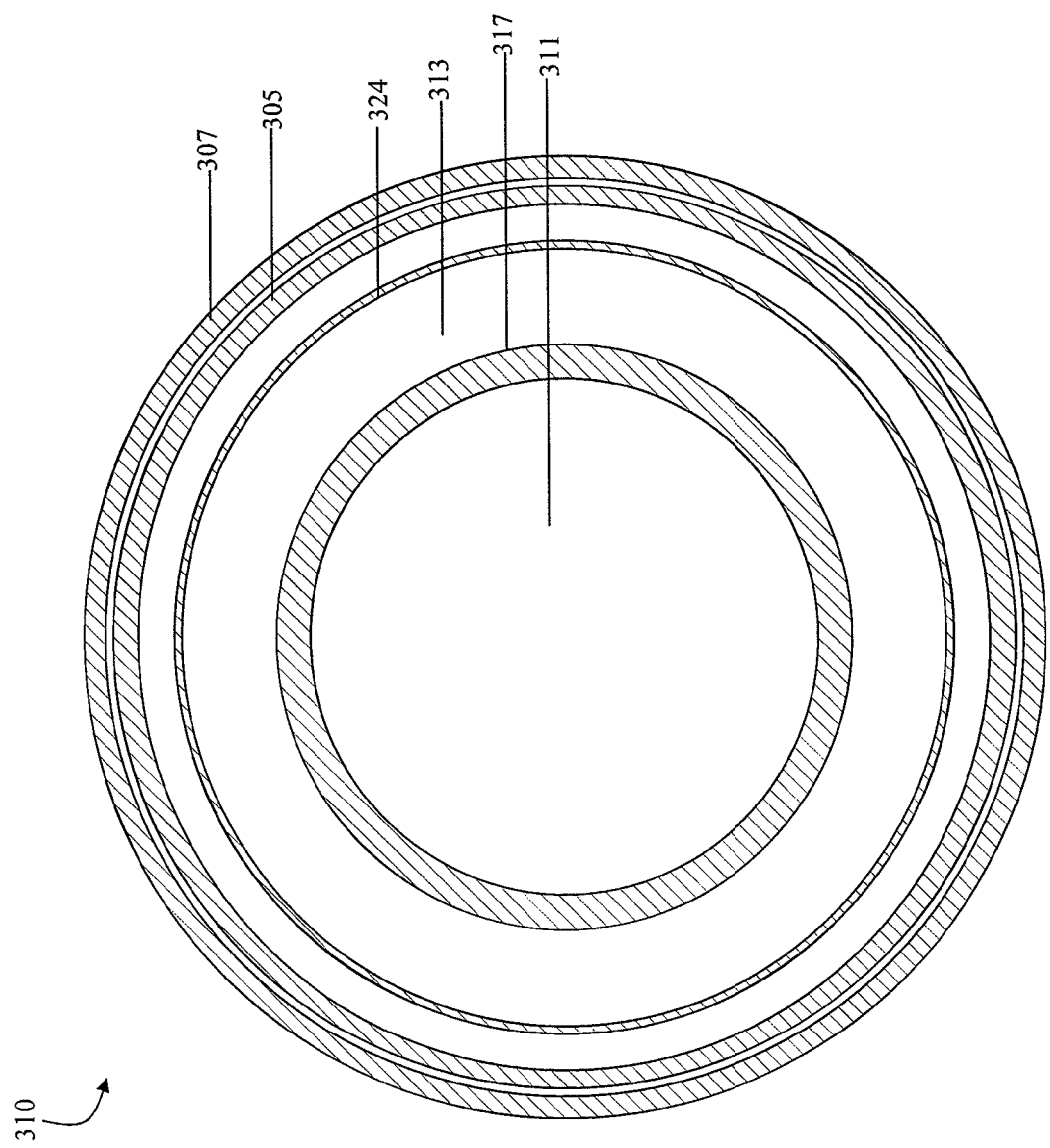

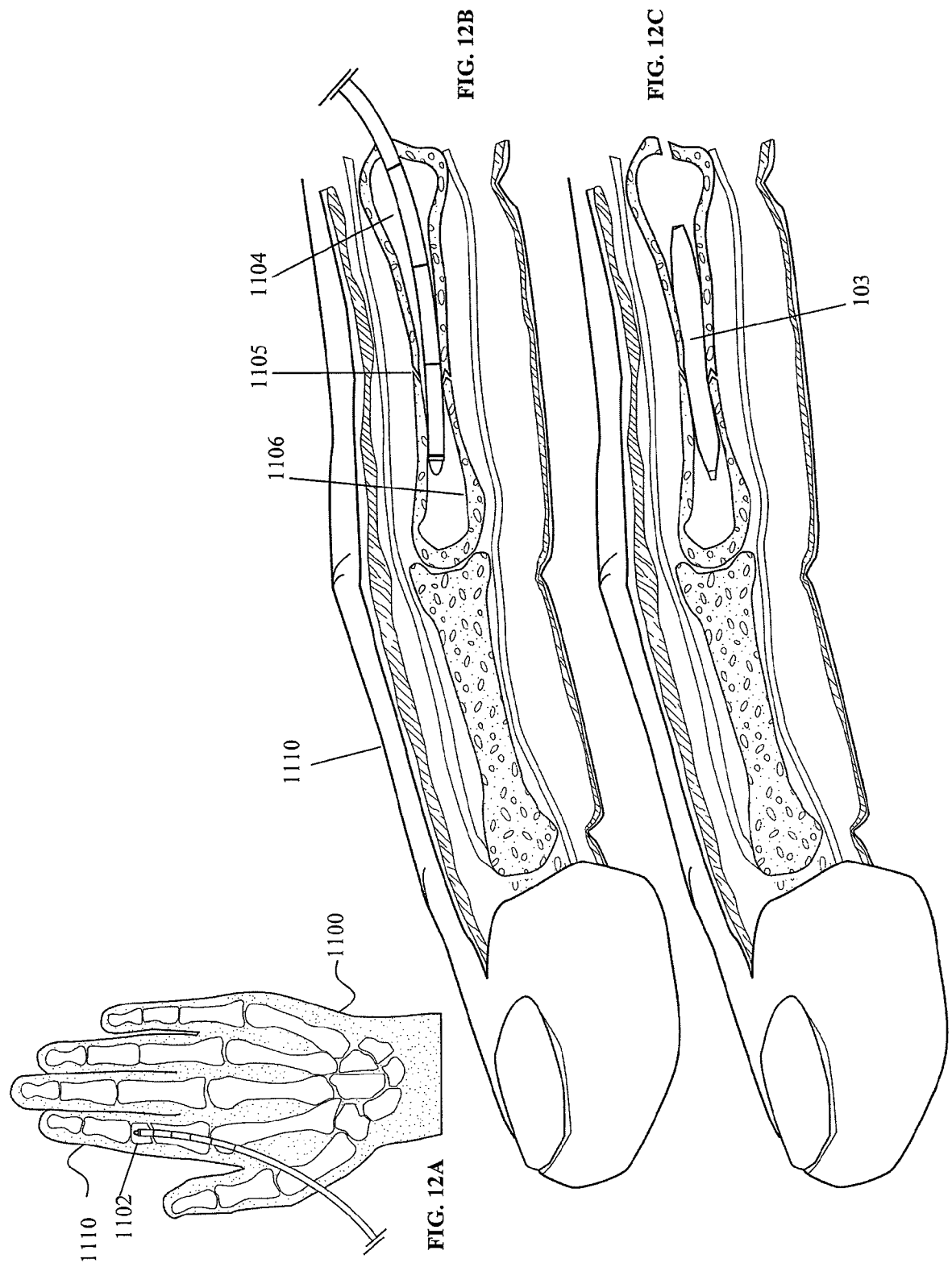

SYSTEMS AND METHODS FOR INTERNAL BONE FIXATION

RELATED APPLICATIONS

This application is a continuation of U.S. application Ser. No. 12/983,496, filed on Jan. 3, 2011, which is a continuation of U.S. application Ser. No. 12/262,411, filed on Oct. 31, 2008, now U.S. Pat. No. 7,879,041, which is a continuation-in-part of U.S. application Ser. No. 11/903,123, filed on Sep. 20, 2007, now U.S. Pat. No. 7,811,284, which claims the benefit of U.S. Provisional Application Ser. No. 60/858,202, filed on Nov. 10, 2006, and which also claims the benefit of U.S. Provisional Application Ser. No. 60/880,646, filed on Jan. 16, 2007, the entirety of these applications are hereby incorporated herein by reference for the teachings therein.

FIELD

The embodiments disclosed herein relate to medical devices for use in repairing a weakened or fractured bone, and more particularly to internal bone fixation devices and methods of using these devices for repairing a weakened or fractured bone.

BACKGROUND

Fracture repair is the process of rejoining and realigning the ends of broken bones. Fracture repair is required when there is a need for restoration of the normal position and function of the broken bone. Throughout the stages of fracture healing, the bones must be held firmly in the correct position and supported until it is strong enough to bear weight. In the event the fracture is not properly repaired, malalignment of the bone may occur, resulting in possible physical dysfunction of the bone or joint of that region of the body.

Until the last century, physicians relied on casts and splints to support the bone from outside the body (external fixation). However, the development of sterile surgery reduced the risk of infection so that doctors could work directly with the bone and could implant materials in the body. Currently there are several internal approaches to repair, strengthen and support a fractured bone. They include the use of internal fixation devices, such as wires, plates, rods, pins, nails, and screws to support the bone directly, and the addition of bone cement mixtures, or bone void fillers to a fractured bone.

The addition of bone cements to a fractured bone for repairing bone and, for example, joining bones are well known in the art. Conventional bone cement injection devices have difficulty adjusting or controlling the injection volume or injection rate of the bone cement in real time in reaction to cancellous bone volume and density conditions encountered inside the fractured bone. Conventional bone cements also may cause complications that include the leakage of the bone cement to an area outside of the fractured bone site, which can result in soft tissue damage as well as nerve root pain and compression.

Thus, there is a need in the art for internal bone fixation devices that repair, strengthen and support a fractured bone using minimally invasive techniques, with ease of use, and minimal damage to the bone and supporting tissues.

SUMMARY

Internal bone fixation devices and methods for using the devices for repairing a weakened or fractured bone are disclosed herein. According to aspects illustrated herein, there is provided a device for repairing a fractured bone that includes a delivery catheter having an elongated shaft with a proximal end, a distal end, and a longitudinal axis therebetween, the delivery catheter having an inner void for passing at least one reinforcing material, and an inner lumen for accepting a light pipe, wherein a distal end of the inner lumen terminates in an optical lens; a conformable member releasably engaging the distal end of the delivery catheter, the conformable member moving from a deflated state to an inflated state when the at least one reinforcing material is delivered to the conformable member; and an adapter releasably engaging the proximal end of the delivery catheter for receiving the light pipe and the at least one reinforcing material.

According to aspects illustrated herein, there is provided a device for use in repairing a fractured bone that includes a delivery catheter having an elongated shaft with a proximal end, a distal end, and a longitudinal axis therebetween, the delivery catheter having an inner void for passing at least one reinforcing material, and an inner lumen for accepting an optical fiber; a conformable member releasably engaging the distal end of the delivery catheter, the conformable member having an inner lumen for accepting the optical fiber, the conformable member moving from a deflated state to an inflated state when the at least one reinforcing material is delivered to the conformable member; and an adapter releasably engaging the proximal end of the delivery catheter for receiving the optical fiber and the at least one reinforcing material.

According to aspects illustrated herein, there is provided a method for repairing a fractured bone that includes gaining access to an inner cavity of the fractured bone; providing a device for use in repairing the fractured bone, the device comprising a delivery catheter having an inner void for passing at least one reinforcing material and an inner lumen for accepting an optical fiber, the delivery catheter releasably engaging a conformable member having an inner lumen for passing the optical fiber; positioning the conformable member spanning at least two bone segments of the fractured bone; inserting the optical fiber into the inner lumen of the conformable member; introducing the at least one reinforcing material through the inner void of the delivery catheter for infusing the reinforcing material within the conformable member, wherein the conformable member moves from a deflated state to an inflated state; activating a light source that is connected to the optical fiber to communicate light energy into the inner lumen of the conformable member such that the at least one reinforcing material is hardened; and releasing the hardened conformable member from the delivery catheter.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A shows a balloon portion of the device in a deflated state. FIG. 2B shows a balloon portion of the device in an inflated state.

FIGS. 3A-3C show close-up views of an embodiment of some of the main components of a device for repairing a weakened or fractured bone of the presently disclosed embodiments. FIG. 3A shows a perspective view of a distal end of the device. FIG. 3B shows a side cross-sectional view taken along line A-A of the device. FIG. 3C shows a cross-sectional view of the device taken along line B-B.

FIG. 5A shows a side cross-sectional view of the device having the light pipe of FIG. 4. FIG. 5B shows a cross-sectional view of the device.

FIGS. 12A-12C shows a device of the presently disclosed embodiments used for internal bone fixation. FIG. 12A shows the placement of the device at a metacarpal fracture in a hand of a patient. FIG. 12B shows a side view of a balloon portion of the device as the balloon portion is inflated with a reinforcing material to repair the fracture. FIG. 12C shows a side view of the balloon portion at the site of the bone fracture after the balloon portion has been released from the device.

Figure 1:
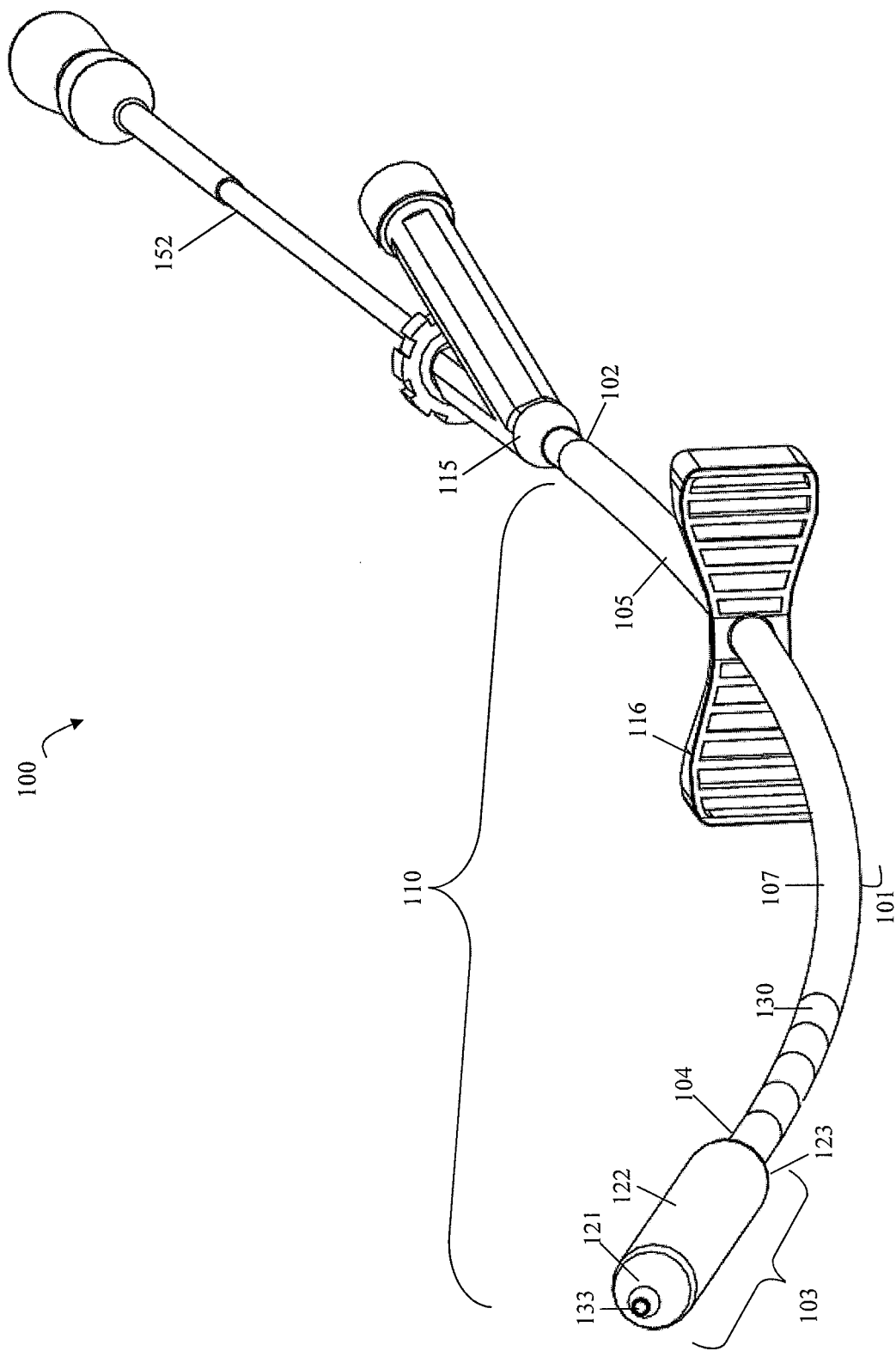
FIG. 1 shows a perspective view of an embodiment of a device for repairing a weakened or fractured bone of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Medical devices and methods for repairing a weakened or fractured bone are disclosed herein. The devices disclosed herein act as internal bone fixation devices and include a delivery catheter having an elongated shaft that terminates in a releasable conformable member. During a procedure for repairing a fractured bone, the conformable member is placed within an inner cavity of a fractured bone in a deflated state. Once in place, the conformable member is expanded from a deflated state to an inflated state by the addition of at least one reinforcing material. The at least one reinforcing material is subsequently hardened within the conformable member using light that travels and disperses from a light pipe that is placed within a light pipe conduit of the device. A light source engaging the light pipe provides the light needed for hardening the reinforcing material. In an embodiment, the light pipe is positioned in the device at a separation junction, which is an area between the releasable conformable member and the elongated shaft of the delivery catheter, to harden the reinforcing material. In an embodiment, the light pipe is positioned in the device such that the light pipe is brought into an inner lumen of the conformable member to harden the reinforcing material. The hardened conformable member may then be released from the delivery catheter and sealed to enclose the at least one reinforcing material within the conformable member. The hardened conformable member remains within the inner cavity of the fractured bone and provides support and proper orientation of the fractured bone resulting in the repair, healing, and strengthening of the fractured bone.

Reinforcing materials include, but are not limited to, bone reinforcing mixtures (such as bone cement mixtures, bone void fillers, epoxies, glues and similar adhesives), orthopedic wires, stainless-steel rods, metal pins, and other similar devices. The reinforcing material may be a natural or synthetic material for strengthening, replacing, or reinforcing of bones or bone tissue. Bone reinforcing mixtures include glues, adhesives, cements, hard tissue replacement polymers, biodegradable polymers such as PLA, PGA, and PLA-PGA copolymers, natural coral, hydroxyapatite, beta-tricalcium phosphate, and various other biomaterials known in the art for strengthening, replacing or reinforcing bones. As inert materials, bone reinforcing mixtures may be incorporated into surrounding tissue or gradually replaced by original tissue. Those skilled in the art will recognize that numerous bone reinforcing mixtures known in the art are within the spirit and scope of the presently disclosed embodiments.

A device disclosed herein may be used for the repair of bones that have weakened or fractured due to any of the bone diseases including, but not limited to osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, scoliosis, and other similar diseases. A device disclosed herein may be used for the repair of bones that have weakened or fractured due to an injury, for example, a fall.

Although some of the figures show the fractured bone as a metacarpal bone in the hand, those skilled in the art will recognize that the disclosed devices and methods may be used for repairing other bones including, but not limited to, the femur, tibia, fibula, humerus, ulna, radius, metatarsals, phalanx, phalanges, ribs, spine, vertebrae, clavicle and other bones and still be within the scope and spirit of the disclosed embodiments.

Figure 2A:
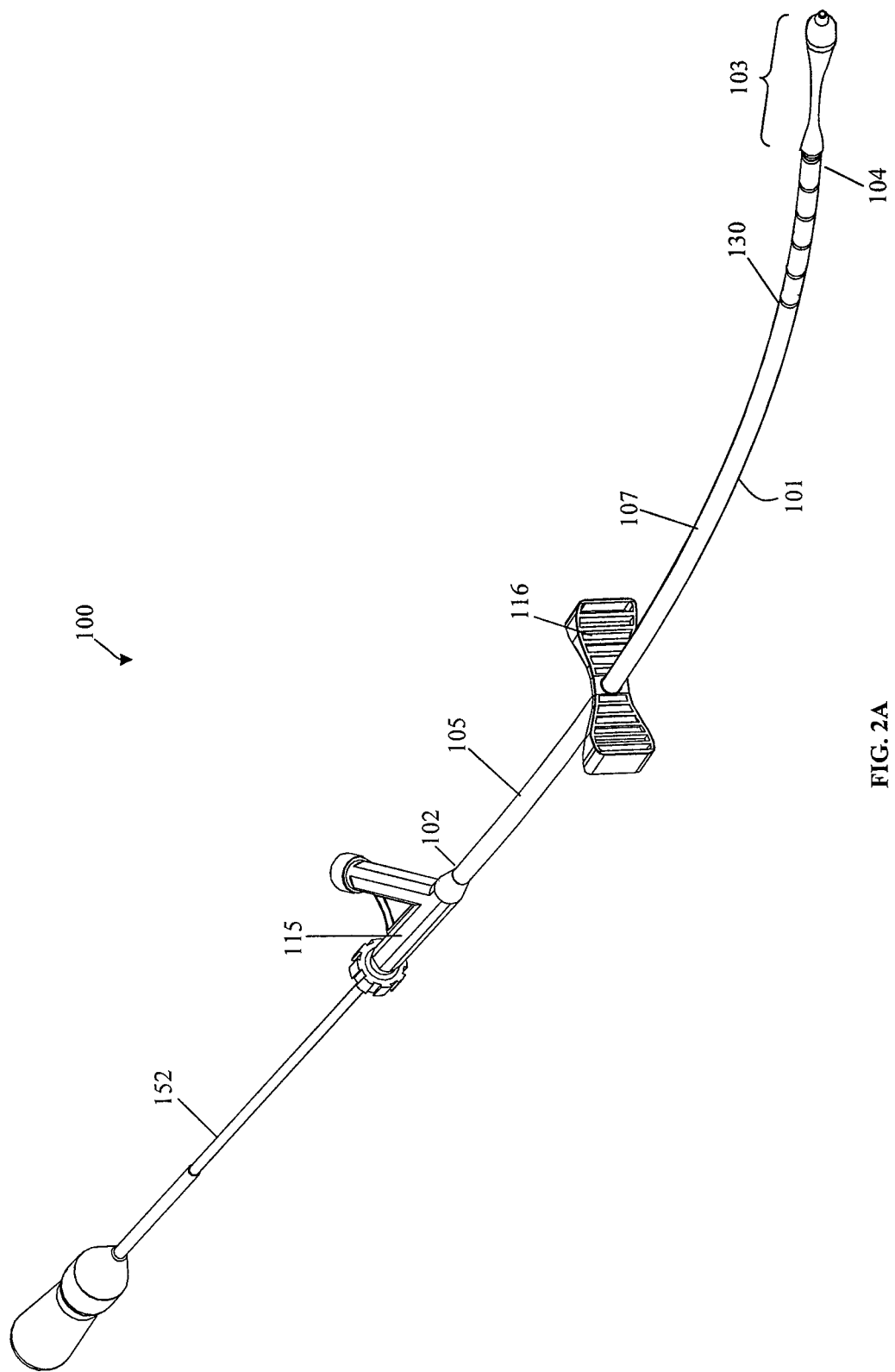
FIGS. 2A-2B show perspective views of the device of FIG. 1 for repairing a weakened or fractured bone of the presently disclosed embodiments.
Figure 2B:
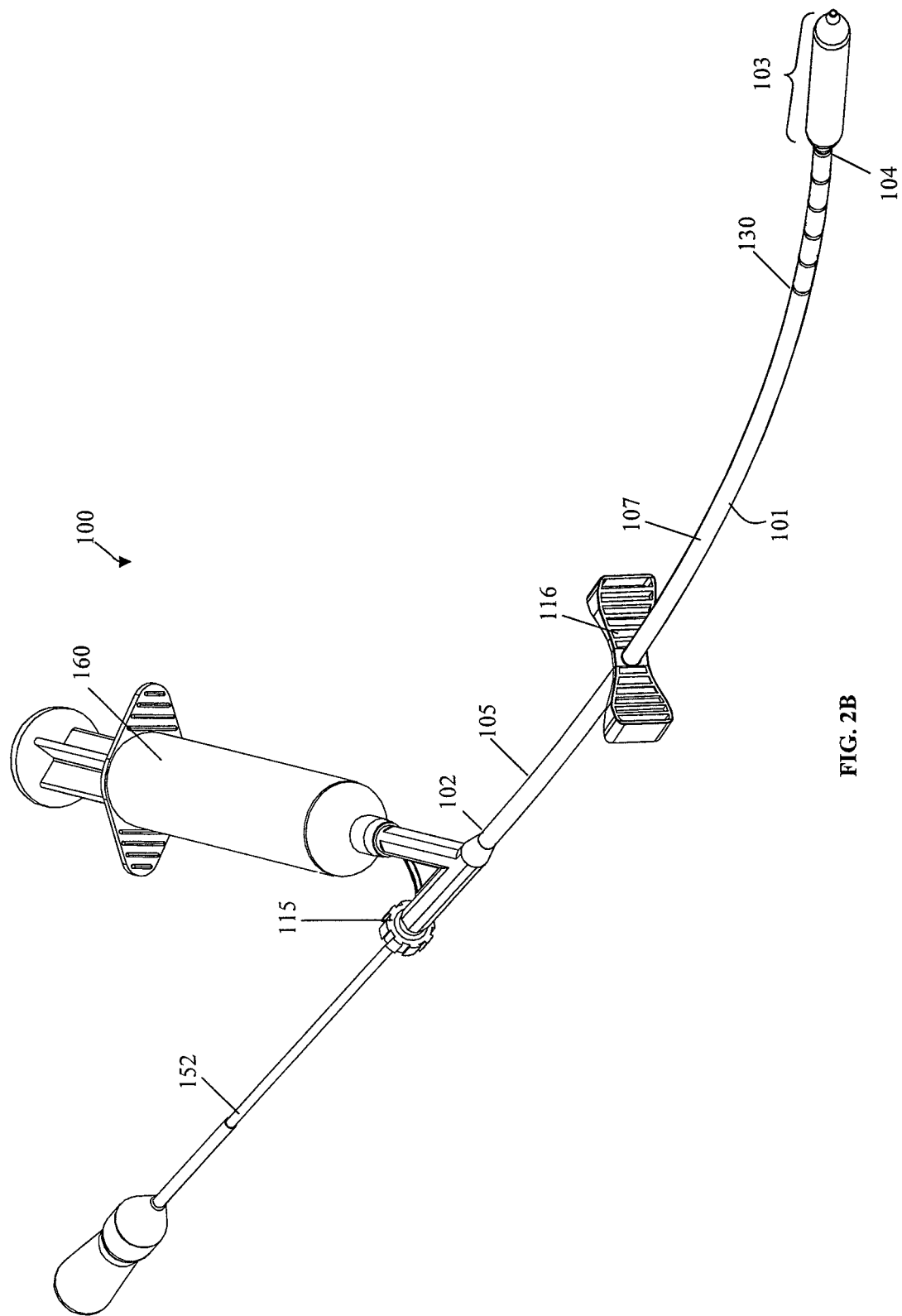

The main components of an embodiment of a device for repairing a weakened or fractured bone are shown generally in FIG. 1 in conjunction with FIG. 2A and FIG. 2B. The device 100 includes a delivery catheter 110 having an elongated shaft 101 with a proximal end 102, a distal end 104, and a longitudinal axis therebetween. In an embodiment, the delivery catheter 110 has a diameter of about 3 mm. The distal end 104 of the delivery catheter 110 terminates in a releasable conformable member 103 (also referred to herein as a balloon portion). The balloon portion 103 may move from a deflated state (FIG. 2A) to an inflated state (FIG. 2B) when at least one reinforcing material is delivered to the balloon portion 103. In an embodiment, the balloon portion 103 has a deflated diameter of about 2.5 mm. In an embodiment, the balloon portion 103 has an inflated diameter ranging from about 4 mm to about 9 mm. The reinforcing material may be delivered to the balloon portion 103 via an inner void capable of allowing the reinforcing material to pass through. In an embodiment, a reinforcing material, such as UV-activated glue, is used to inflate and deflate the balloon portion 103. In an embodiment, the balloon portion 103 may be round, flat, cylindrical, oval, rectangular or another shape. The balloon portion 103 may be formed of a pliable, resilient, conformable, and strong material, including but not limited to urethane, polyethylene terephthalate (PET), nylon elastomer and other similar polymers. In an embodiment, the balloon portion 103 is constructed out of a PET nylon aramet or other non-consumable materials. PET is a thermoplastic polymer resin of the polyester family that is used in synthetic fibers. Depending on its processing and thermal history, PET may exist both as an amorphous and as a semi-crystalline material. Semi-crystalline PET has good strength, ductility, stiffness and hardness. Amorphous PET has better ductility, but less stiffness and hardness. PET can be semi-rigid to rigid, depending on its thickness, and is very lightweight. PET is strong and impact-resistant, naturally colorless and transparent and has good resistance to mineral oils, solvents and acids.

In an embodiment, the balloon portion 103 is designed to evenly contact an inner wall of a cavity in a bone. In an embodiment, the balloon portion 103 may have a pre-defined shape to fit inside the cavity in a particularly shaped bone. For example, as depicted in the embodiment of FIG. 1, the pre-defined shape of the balloon portion 103 may be an elongated cylinder. The balloon portion 103 has a proximal end 123, a distal end 121 and a longitudinal axis therebetween having an outer surface 122. In an embodiment, the outer surface 122 of the balloon portion 103 is substantially even and smooth and substantially mates with a wall of the cavity in the bone. In an embodiment, the outer surface 122 of the balloon portion 103 is not entirely smooth and may have some small bumps or convexity/concavity along the length. In some embodiments, there are no major protuberances jutting out from the outer surface 122 of the balloon portion 103. The balloon portion 103 may be designed to remain within the cavity of the bone and not protrude through any holes or cracks in the bone. In an embodiment, the outer surface 122 of the balloon portion 103 may be flush with the wall of the cavity and when the balloon portion 103 is inflated, the outer surface 122 may contact the wall of the cavity along at least a portion of the surface area. In an embodiment, when the balloon portion 103 is inflated, a majority or all of the balloon's 103 outer surface 122 does not contact the wall of the cavity and does not extend through any holes or cracks in the bone.

The outer surface 122 of the balloon portion 103 may be coated with materials such as drugs, bone glue, proteins, growth factors, or other coatings. For example, after a minimally invasive surgical procedure an infection may develop in a patient, requiring the patient to undergo antibiotic treatment. An antibiotic drug may be added to the outer surface 122 of the balloon portion 103 to prevent or combat a possible infection. Proteins, such as, for example, the bone morphogenic protein or other growth factors have been shown to induce the formation of cartilage and bone. A growth factor may be added to the outer surface 122 of the balloon portion 103 to help induce the formation of new bone. Due to the lack of thermal egress of the reinforcing material in the balloon portion 103, the effectiveness and stability of the coating is maintained.

In an embodiment, the outer surface 122 of the balloon portion 103 may have ribs, ridges, bumps or other shapes to help the balloon portion 103 conform to the shape of a bone cavity. Balloons may be constructed to achieve transit within luminal cavities of bones and to expand, manipulate, and remove obstructions. In this way, the balloon portion 103 may slide easier within the luminal bodies without coming in contact with surrounding tissue. The balloon portion 103 may also be designed to be placed in a bone and to grab a fractured bone without any slippage using a textured surface with a variety of shapes such as small ridges or ribs.

In an embodiment, a water soluble glue is applied to the outer surface 122 of the balloon portion 103. When the balloon portion 103 is expanded and engages a moist bone, the water soluble glue on the outer surface 122 of the balloon portion 103 becomes sticky or tacky and acts as a gripping member to increase the conformal bond of the balloon portion 103 to the bone. Once the balloon portion 103 is inflated, the outer surface 122 of the balloon portion 103 grips the bone forming a mechanical bond as well as a chemical bond. These bonds prevent the potential for a bone slippage. The water soluble glue may be cured by any light (e.g., UV not required).

In an embodiment, the balloon portion 103 has a textured surface which provides one or more ridges that allow grabbing all portions of bone fragments of a fractured bone. In an embodiment, ridges are circumferential to the balloon portion 103 and designed to add more grab to the inflated balloon portion 103 on contact with the fractured bone. The ridges are also compressive so the ridges fold up on the fractured bone when the balloon portion 103 is completely inflated. In an embodiment, sand blasted surfacing on the outer surface 122 of the balloon portion 103 improves the connection and adhesion between the outer surface 122 of the balloon portion 103 and the inner bone. The surfacing significantly increases the amount of surface area that comes in contact with the bone resulting in a stronger grip.

The balloon portion 103 of the device 100 typically does not have any valves. One benefit of having no valves is that the balloon portion 103 may be inflated or deflated as much as necessary to assist in the fracture reduction and placement. Another benefit of the balloon portion 103 having no valves is the efficacy and safety of the device 100. Since there is no communication passage of reinforcing material to the body there cannot be any leakage of material because all the material is contained within the balloon portion 103. In an embodiment, a permanent seal is created between the balloon portion 103 that is both hardened and affixed prior to the delivery catheter 110 being removed. The balloon portion 103 may have valves, as all of the embodiments are not intended to be limited in this manner.

The balloon portion 103 of the delivery catheter 110 has a diameter ranging from about 5 mm to about 9 mm. The balloon portion 103 of the delivery catheter 110 has a length ranging from about 20 mm to about 80 mm. In an embodiment, the balloon portion 103 has a diameter of about 5 mm and a length of about 30 mm. In an embodiment, the balloon portion 103 has a diameter of about 5 mm and a length of about 40 mm. In an embodiment, the balloon portion 103 has a diameter of about 6 mm and a length of about 30 mm. In an embodiment, the balloon portion 103 has a diameter of about 6 mm and a length of about 40 mm. In an embodiment, the balloon portion 103 has a diameter of about 6 mm and a length of about 50 mm. In an embodiment, the balloon portion 103 has a diameter of about 7 mm and a length of about 30 mm. In an embodiment, the balloon portion 103 has a diameter of about 7 mm and a length of about 40 mm. In an embodiment, the balloon portion 103 has a diameter of about 7 mm and a length of about 50 mm.

In an embodiment, a stiffening member 105 surrounds the elongated shaft 101 of the delivery catheter 110, and provides rigidity over the elongated shaft 101. A pusher or stabilizer 116 can be loaded proximal to the balloon portion 103. A slip sleeve 107 can surround the stiffening member 105. In an embodiment, the slip sleeve 107 surrounds the stiffening member 105 from the proximal end 123 of the balloon portion 103 up until the pusher 116. One or more radiopaque markers or bands 130 may be placed at various locations along the balloon portion 103 and/or the slip sleeve 107. A radiopaque ink bead 133 may be placed at the distal end 121 of the balloon portion 103 for alignment of the device 100 during fluoroscopy. The one or more radiopaque bands 130, using radiopaque materials such as barium sulfate, tantalum, or other materials known to increase radiopacity, allows a medical professional to view the device 100 using fluoroscopy techniques. The one or more radiopaque bands 130 also provide visibility during inflation of the balloon portion 103 to determine the precise positioning of the balloon portion 103 and the device 100 during placement and inflation. The one or more radiopaque bands 130 permit visualization of any voids that may be created by air that gets entrapped in the balloon portion 103. The one or more radiopaque bands 130 permit visualization to preclude the balloon portion 103 from misengaging or not meeting the bone due to improper inflation to maintain a uniform balloon/bone interface.

In an embodiment, an adapter 115, such as a Tuohy-Borst adapter, engages the proximal end 102 of the delivery catheter 110. A light pipe 152 having a connector 150 for communicating light from a light source (not shown), can be introduced into one of the side-arms of the adapter 115 and passes within an inner lumen of the delivery catheter 110. In an embodiment, the light pipe 152 is an optical fiber. The optical fiber can be made from any material, such as glass, silicon, silica glass, quartz, sapphire, plastic, combinations of materials, or any other material, and may have any diameter. In an embodiment, the optical fiber is made from silica glass and may have wide-angle light dispersion of about 88 degrees. In an embodiment, the optical fiber is made from a plastic material. An adhesive system housing the reinforcing material may be introduced into another side-arm of the adapter 115, as shown in FIG. 2B. Alternately, a Luer fitting may engage the proximal end 102 of the delivery catheter 110 and a Luer fitting would exist on the light pipe 152 such that the delivery catheter 110 and the light pipe 152 would lock together.

Examples of adhesive systems include, but are not limited to, caulking gun type systems, syringe systems, bag systems that contain the bone reinforcing material where the delivery of the bone reinforcing material is controlled using a tube clamp or any other restrictor valve. In the embodiment shown in FIG. 2B, the adhesive system is a syringe 160. In an embodiment, the syringe 160 has a control mechanism that regulates the flow of the reinforcing material. The control mechanism of the syringe 160 allows the reinforcing material to flow into the delivery catheter 110 and the flow may be stopped if desired. The syringe 160 makes direct contact to control the directional flow of the reinforcing material, and the direction of flow of the reinforcing material instantaneously changes within the delivery catheter 110 in response to a change in the direction of the syringe 160.

In an embodiment, the syringe 160 is opaque and does not allow light to penetrate within the syringe 160. Having an opaque syringe 160 ensures that the reinforcing material contained in the syringe 160 is not exposed to light and will not cure in the syringe 160. The reinforcing material is of a liquid consistency, as measured in Centipoise (cP), the unit of dynamic viscosity, so the reinforcing material may be infused from the syringe 160 into the delivery catheter 110 and into the balloon portion 103. Because the reinforcing material has a liquid consistency and is viscous, the reinforcing material may be delivered using low pressure delivery and high pressure delivery is not required, but may be used.

In an embodiment, the reinforcing material is a light cure adhesive or ultraviolet (UV) adhesive. Examples of light cured materials include those commercially available from Loctite of Henkel Corporation, located in Rocky Hill, Conn. and those commercially available from DYMAX Corporation, located in Torrington, Conn. A benefit of UV curing is that it is a cure-on-demand process and that adhesives may be free of solvents and include environmentally friendly resins that cure in seconds upon exposure to long wave UV light or visible light. Different UV adhesives use photoinitiators sensitive to different ranges of UV and visible light. Being very energetic, UV light can break chemical bonds, making molecules unusually reactive or ionizing them, in general changing their mutual behavior. Visible light, for example, visible blue light, allows materials to be cured between substrates that block UV light but transmits visible light (e.g., plastics). Visible light penetrates through the adhesive to a greater depth. Since the visible light penetrates through the adhesive, curing of the adhesive increases as a greater portion of the electromagnetic spectrum is available as useful energy. Additives may be used with the UV adhesive delivery system, including, but not limited to drugs (for example, antibiotics), proteins (for example, growth factors) or other natural or synthetic additives.

The electromagnetic spectrum is the range of all possible electromagnetic radiation. The electromagnetic spectrum of an object is the frequency range of electromagnetic radiation that the object emits, reflects, or transmits. The electromagnetic spectrum extends from just below the frequencies used for modern radio (at the long-wavelength end) to gamma radiation (at the short-wavelength end), covering wavelengths from thousands of kilometers down to fractions of the size of an atom. In an embodiment, the UV adhesive is a single-component, solvent-free adhesive that will not cure until a UV light engages the adhesive, and when that occurs, the adhesive will cure in seconds to form a complete bond with a shear strength. In an embodiment, the UV adhesive is a single-component, solvent-free adhesive that will not cure until a visible light engages the adhesive, and when that occurs, the adhesive will cure in seconds to form a complete bond with a shear strength. In an embodiment, the reinforcing material exhibits a shrinkage upon cure of about 2 to about 3 percent.

UV light wavelength ranges from about 1 nm to about 380 nm, and can be subdivided into the following categories: near UV (380-200 nm wavelength; abbreviated NUV), far or vacuum UV (200-10 nm; abbreviated FUV or VUV), and extreme UV (1-31 nm; abbreviated EUV or XUV). Similarly, visible light has a wavelength spectrum of between about 380 to about 780 nm. Those skilled in the art will recognize that some UV adhesives may be activated by UV light, visible light, x-rays, gamma rays, microwaves, radio waves, long waves or any light having a wavelength less than about 1 nm, between about 1 nm and about 380 nm, between about 380 nm and about 780 nm, or greater than 780 nm, as not all embodiments are intended to be limited in that respect.

Using a UV light, the reinforcing material ensures there is no or minimal thermal egress and that the thermal egress may not be long in duration. More specifically, there is no chemical composition or mixing of materials. Using the UV light to cure the reinforcing material assists in holding broken bones in place, filling of the balloon portion, and viewing under a C arm imaging system. The reinforcing materials cure in such a way that is sufficient to hold a bone in the correct orientation. More specifically, the ability to inflate, set, adjust, orient bones, and the resulting union of the bone are available prior to hardening the reinforcing material. The introduction of the UV light starts the photoinitiator and the UV adhesive hardens. Once the UV light is introduced, the adhesive inside the balloon portion hardens and the adhesives inside are affixed in place. Until the UV light is introduced, the bone placement is not disturbed or rushed as there is no hardening of the adhesives until the light is introduced, the balloon portion may be inflated or deflated due to the viscosity of the adhesive. The adhesive may be infused or removed from the balloon portion due to the low viscosity of the adhesive. In an embodiment, the viscosity of the reinforcing material has a viscosity of about 1000 cP or less. In an embodiment, the reinforcing material has a viscosity ranging from about 650 cP to about 450 cP. Not all embodiments are intended to be limited in this respect and some embodiments may include reinforcing materials having a viscosity exactly equal to or greater than 1000 cP. In an embodiment, a contrast material may be added to the reinforcing material without significantly increasing the viscosity. Contrast materials include, but are not limited to, barium sulfate, tantalum, or other contrast materials known in the art.

Several epoxies known in the art are suitable for use as bone reinforcing materials and vary in viscosity, cure times, and hardness (durometer or shore) when fully cured. A durometer of a material indicates the hardness of the material, defined as the material's resistance to permanent indentation. Depending on the amount of resultant support that is necessary for a given bone fracture, a specific durometer UV adhesive may be chosen. Alternately, multiple UV adhesives having varying durometers may be chosen for the repair of a bone fracture and be within the scope and spirit of the presently disclosed embodiments. The durometer of a material may be altered to achieve either greater rigidity or a more malleable result. The mechanical properties of the epoxies may dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

In an embodiment, the reinforcing material is cured by chemical activation or thermal activation. Chemical activation includes but is not limited to water or other liquids. In an embodiment, the reinforcing material is a drying adhesive which has a polymer dissolved in a solvent such that as the solvent evaporates, the adhesive hardens. In an embodiment, the reinforcing material is a hot or thermoplastic adhesive such that as the adhesive cools, the adhesive hardens.

The reinforcing material is not limited to the embodiments described herein and may be any material that reinforces the bone. Some materials may require or be enhanced by curing via any means, such as UV or visible light, heat, and/or addition or removal of a chemical or substance, may utilize any outside or internal processes to cure the material, or may not require curing.

In an embodiment, carbon nanotubes (CNTs) are added to the reinforcing material to increase the strength of the material. Carbon nanotubes are an allotrope of carbon that take the form of cylindrical carbon molecules and have novel strength properties. Carbon nanotubes exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the reinforcing materials.

In an embodiment, a separation area is located at the junction between the proximal end 123 of the balloon portion 103 and the elongated shaft 101. The separation area may also include an illumination band. When activated, the illumination band causes light to cure the reinforcing material located in the balloon portion 103 within the illumination band. The illumination band extends around the delivery catheter 110 and has a stress concentrator. The stress concentrator may be a notch, groove, channel or similar structure that concentrates stress in the illumination band. The stress concentrator of the illumination band may be notched, scored, indented, pre-weakened or pre-stressed to direct separation of the balloon portion 103 from the elongated shaft 101 of the delivery catheter 110 under specific torsional load. The separation area ensures that there are no leaks of reinforcing material from the elongated shaft 101 of the delivery catheter 110 and/or the balloon portion 103. The separation area seals the balloon portion 103 and removes the elongated shaft 101 of the delivery catheter 110 by making a break at a known or predetermined site (e.g., a separation area). The separation area may be various lengths and up to about an inch long. When torque (twisting) is applied to the delivery catheter 110, the elongated shaft 101 separates from the balloon portion 103. The twisting creates a sufficient shear to break the residual reinforcing material and create a clean separation of the balloon/shaft interface. The illumination band may be connected to the light source and may be activated by a separate switch. Having a distinct switch to activate the illumination band may help to prevent inadvertent delivery of light from the light pipe to cure the reinforcing material. The activation of the illumination band seals the balloon portion 103 and seals the end of the delivery catheter 110, and ensures that there is a "hard seal" of the reinforcing material at the illumination band allowing no reinforcing material to leak from the balloon portion 103 or the delivery catheter 110.

Figure 3A:
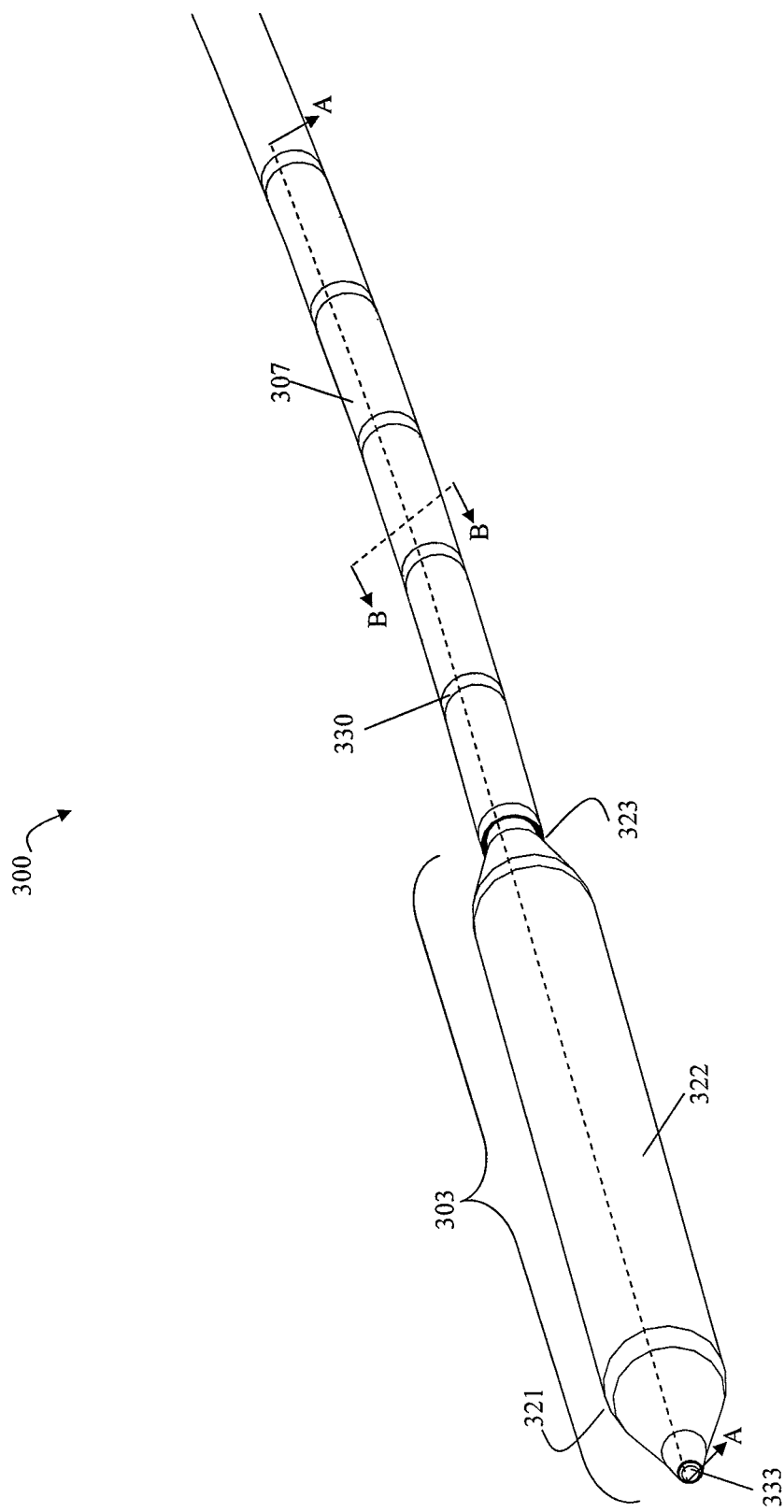
Figure 3B:
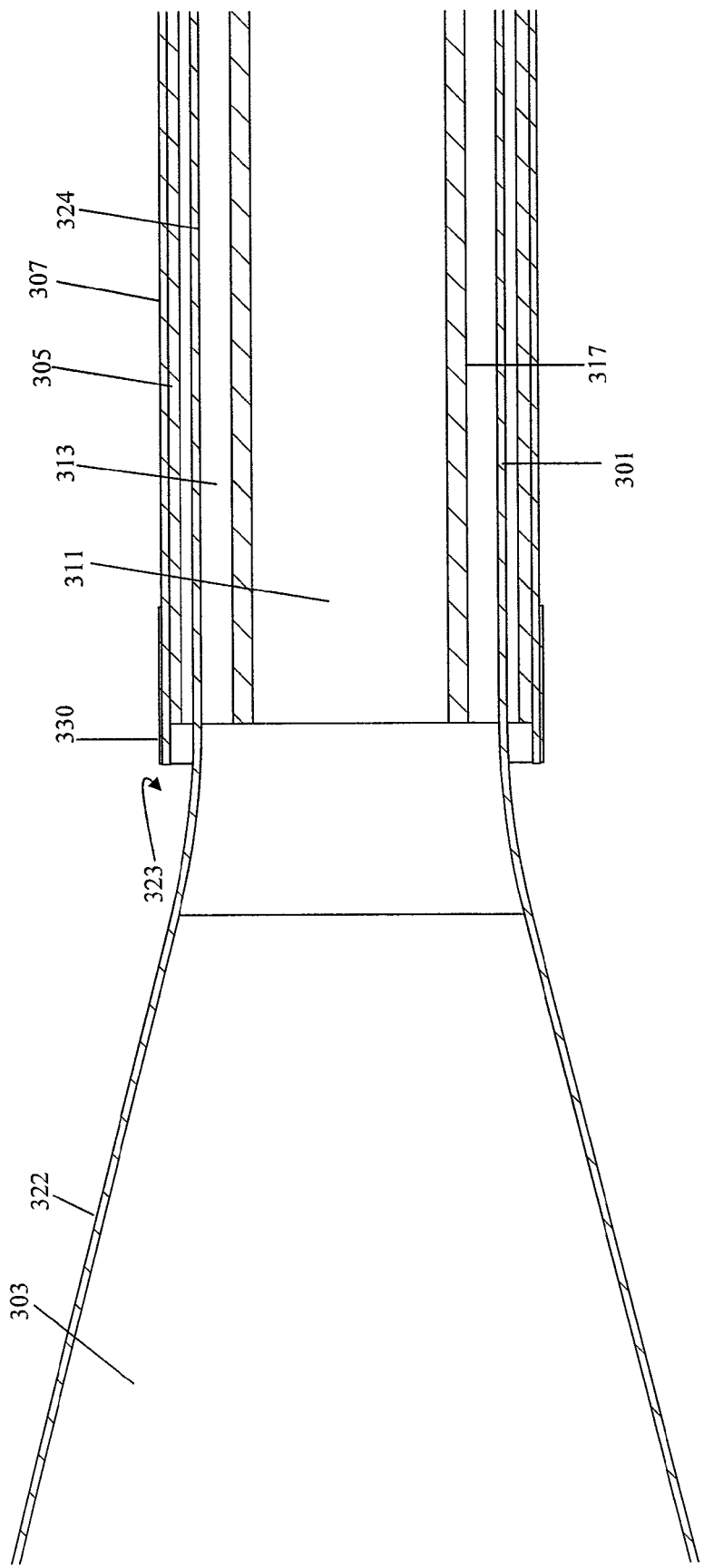

FIG. 3A, FIG. 3B and FIG. 3C show close-up views of an embodiment of some of the main components of a device 300 for repairing a weakened or fractured bone of the presently disclosed embodiments. One or more radiopaque markers or bands 330 are placed at various locations along a slip sleeve 307 of a delivery catheter 310 of the device 300. Those skilled in the art will recognize that radiopaque markers 330 may also be placed at various locations along a balloon portion 303 of the device 300. In an embodiment, the one or more radiopaque bands 330 are placed at intervals of about 10 mm along the length of a slip sleeve 307 of the device 300. In an embodiment, a radiopaque ink bead 333 is placed at a distal end 321 of the balloon portion 303 for easy visualization and alignment of the device 300 by fluoroscopy during a repair procedure. The radiopaque markers 330 and radiopaque ink bead 333 are formed using radiopaque material such as barium sulfate, tantalum, or other materials known to increase radiopacity. The radiopaque markers 330 provide visibility during inflation of the balloon portion 303 to determine the precise positioning of the balloon portion 303 and the delivery catheter 310 during placement and inflation. The radiopaque markers 330 permit visualization of voids created by air that may be entrapped in the balloon portion 303. The radiopaque markers 330 permit visualization to preclude the balloon portion 303 from mis-engaging or not meeting the surface of a bone due to improper inflation. Once the correct positioning of the balloon portion 303 and delivery catheter 310 are determined, the proximal end of the delivery catheter 310 may be attached to a delivery system that contains a reinforcing material.

A cross-sectional view taken along line A-A of FIG. 3A is shown in FIG. 3B. As shown in FIG. 3B, an elongated shaft 301 of the delivery catheter 310 terminates in the balloon portion 303 having an outer surface 322. Within the elongated shaft 301 of the delivery catheter 310 is a light pipe conduit 311 for accepting a light pipe (not shown). A void 313 for passage of a reinforcing material is formed between an inner surface 324 of the delivery catheter 310 and an outer surface 317 of the light pipe conduit 311. A delivery system comprising the reinforcing material may be attached to a side arm of a Tuohy-Borst adapter that is engaged to a proximal end of the delivery catheter 310. The reinforcing material may pass through the void 313 of the delivery catheter 310 and enter the balloon portion 303. The infusion of the reinforcing material causes the balloon portion 303 to inflate to a desired state. In an embodiment, the reinforcing material is infused through the void 313 in the delivery catheter 310 to expand the balloon portion 303 to position a bone in a healing orientation. To establish the healing orientation, the balloon portion 303 inflates until the bones move into an aligned orientation and are supported. Orientation of the bones may be done without any visualization of the process or using x-ray or a fluoroscope. In an embodiment, a C arm imaging system is used as part of a fluoroscope. The C arm imaging system may allow movement or manipulation of the fluoroscope to rotate around tissue while viewing. Other techniques may be used for monitoring or inspecting the expansion of the balloon portion 303 such as magnetic resonance imaging (MRI), ultrasound imaging, x-ray fluoroscopy, Fourier transform infrared spectroscopy, ultraviolet or visible spectroscopy. The balloon portion 303 may be composed of non ferromagnetic materials and, thus, is compatible with MRI.

A cross-sectional view taken along line B-B of FIG. 3A is shown in FIG. 3C. As shown in FIG. 3C, the outer slip sleeve 307 surrounds the stiffening member 305. The stiffening member 305 surrounds and provides rigidity to the elongated shaft of the delivery catheter 310. The light pipe conduit 311 provides a space for a light pipe to pass through. The void 313 is formed between the outer surface 317 of the light pipe conduit 311 and the inner surface 324 of the delivery catheter 310. This void 313 provides a passageway for the reinforcing material. The outer surface 317 of the light pipe conduit 311 allows for a separation between the light pipe and the reinforcing material.

Figure 4:
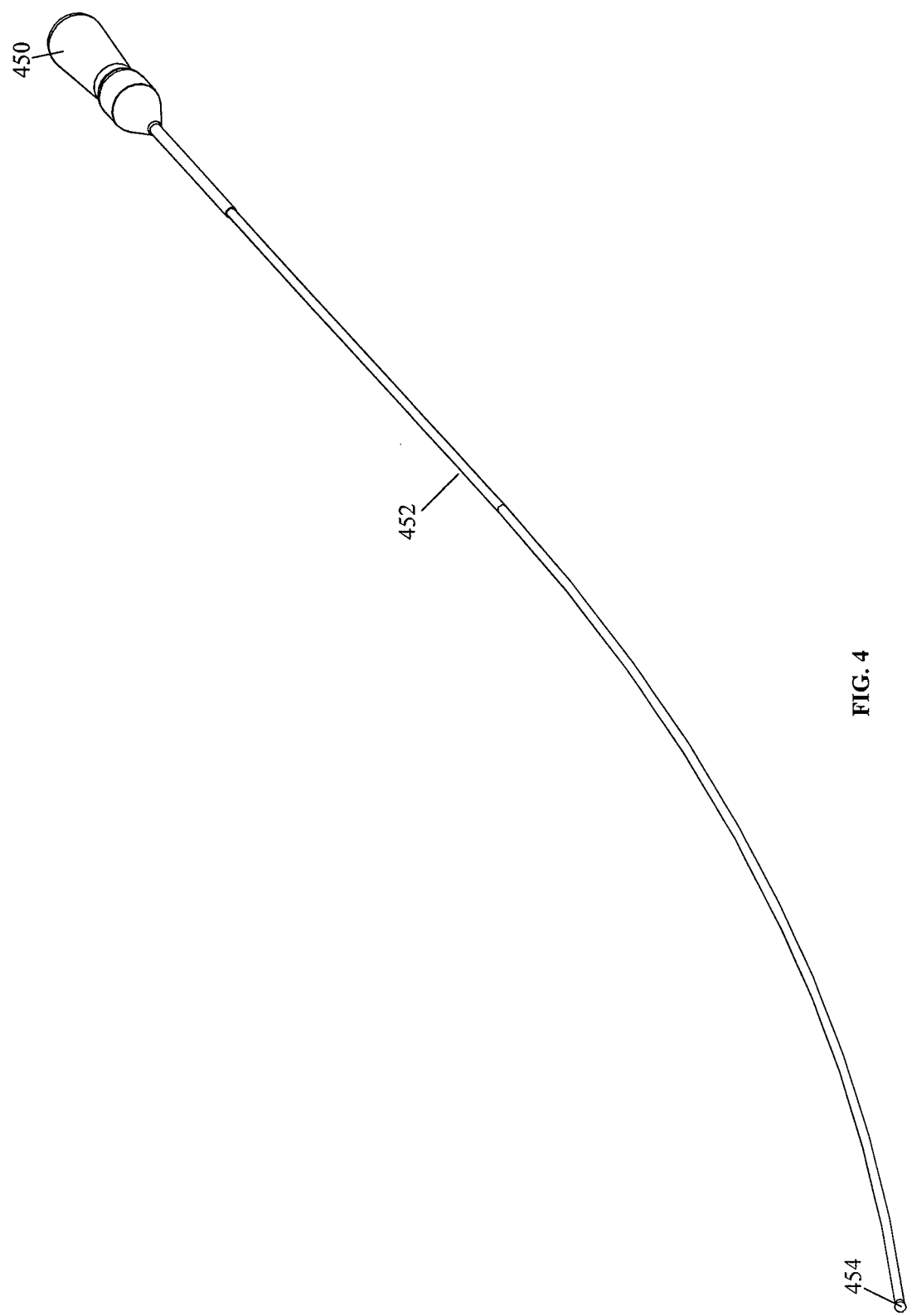
FIG. 4 shows a perspective view of an embodiment of a light pipe for use with a device for repairing a weakened or fractured bone of the presently disclosed embodiments.

FIG. 4 shows an embodiment of a light pipe 452 for use with a device for repairing a weakened or fractured bone of the presently disclosed embodiments. The light pipe 452 is connected to a light source (not shown) through a connector 450. Light emitted by the light pipe 452 is used to harden the reinforcing material that has been infused into a balloon portion of a delivery catheter of the device. In the embodiment depicted in FIG. 4, the light pipe 452 terminates in an optical lens 454. Energy emitted from the light pipe 452 is projected through the optical lens 454 and guided into the balloon portion of the delivery catheter of the device. The optical lens 454 may be convex, concave or planar. The optical lens 454 can converge or diverge the transmitted energy from the light pipe 452. In an embodiment, the optical lens 454 is made out of a plastic material such as Acrylic (PMMA), Polycarbonate (PC), Polystyrene (PS), or other similar materials known to those in the art such as Cyclic Olefin Copolymer (COC), and Amorphous Polyolefin (Zeonex). In an embodiment, the optical lens 454 is made out of a glass material such as quartz.

The light pipe 452 is introduced into a side arm of an adapter that engages a proximal end of the delivery catheter of the device. The light pipe 452 runs through an elongated shaft of the delivery catheter of the device, through the light pipe conduit. In an embodiment, the light pipe 452 will be positioned within the light pipe conduit such that it is positioned within a separation area of the device. The separation area is located at a junction between a distal end of the balloon portion and the elongated shaft. Activation of a light source, which connects to the light pipe 452 through connector 450, communicates light down the light pipe 452 to cure the reinforcing material resulting in the affixing of the balloon portion in an expanded shape. A cure may refer to any chemical, physical, and/or mechanical transformation that allows a composition to progress from a form (e.g., flowable form) that allows it to be delivered through the void in the delivery catheter, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

Figure 5A:
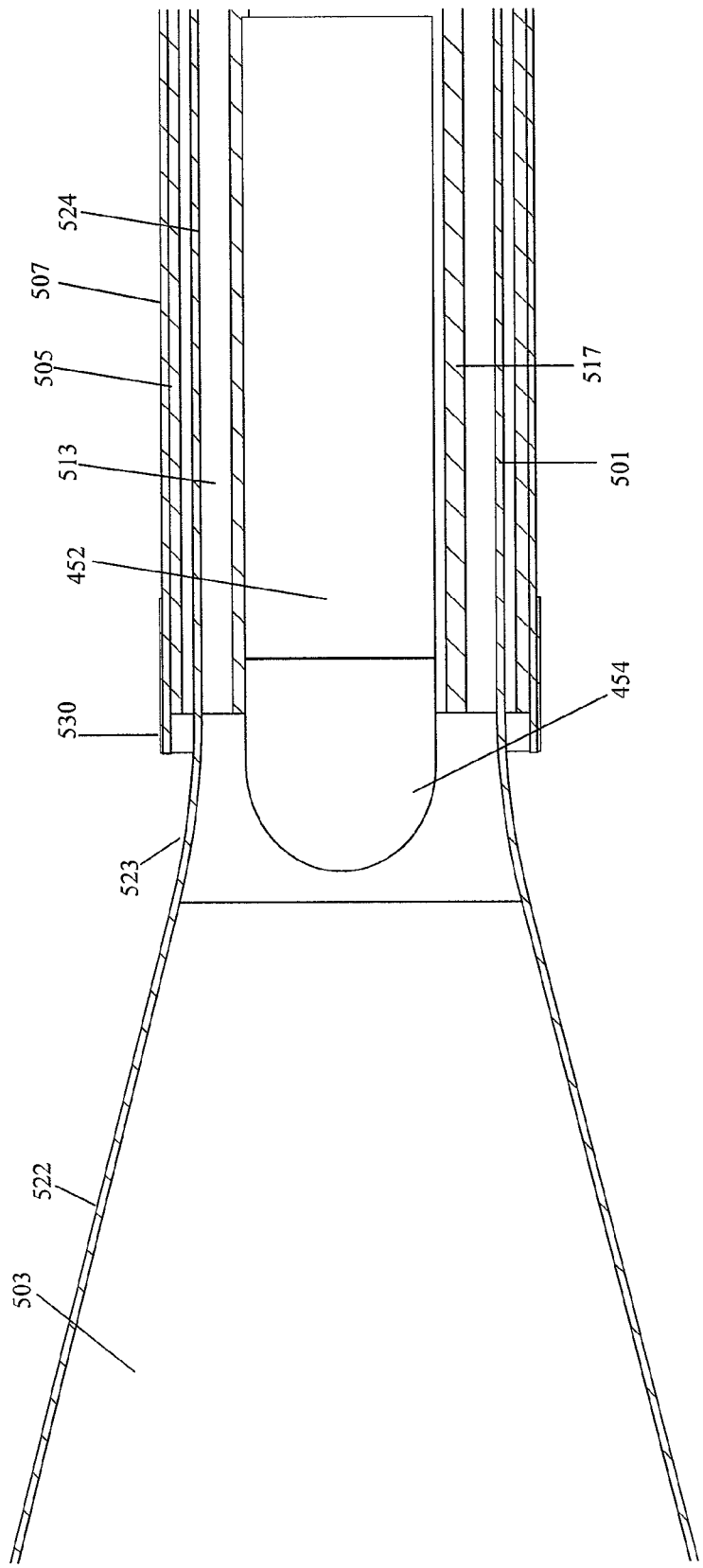
FIGS. 5A-5B show cross-sectional views of an embodiment of a device for repairing a weakened or fractured bone of the presently disclosed embodiments.
Figure 5B:
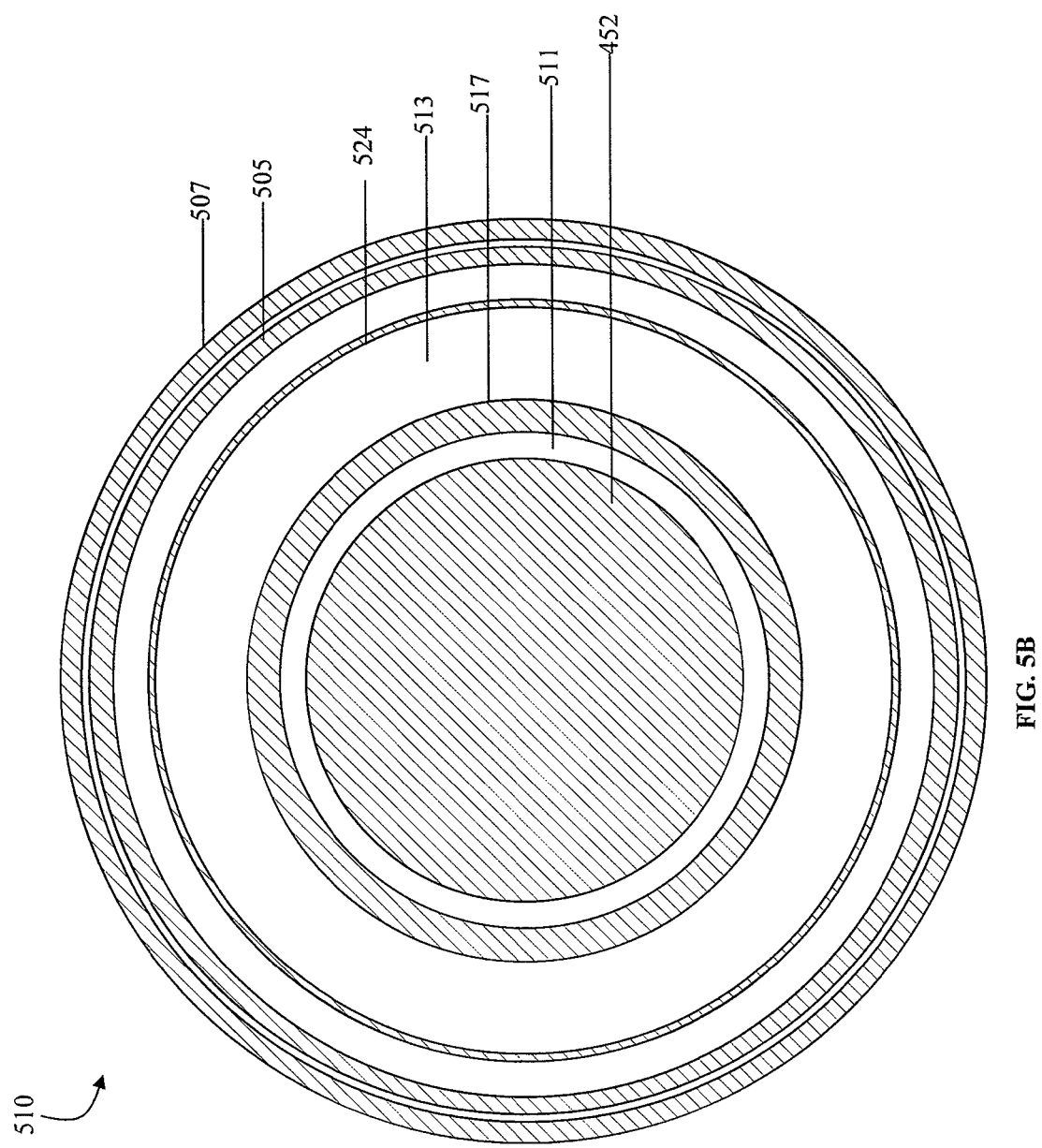

FIG. 5A and FIG. 5B show side cross-sectional views of an embodiment of some of the main components of a device for repairing a fractured bone having the light pipe 452 of FIG. 4 passing through a light pipe conduit 511 of an elongated shaft 501 of the device. The light pipe 452 is used to communicate light towards a balloon portion 503 of the device, and to harden reinforcing material that has been infused into the balloon portion 503 of the device. Energy emitted from the light pipe 452 is projected through the optical lens 454 and guided into the balloon portion 503. The optical lens 454 may be convex, concave or planar. The optical lens 454 can converge or diverge the transmitted energy from the light pipe 452.

Figure 6:
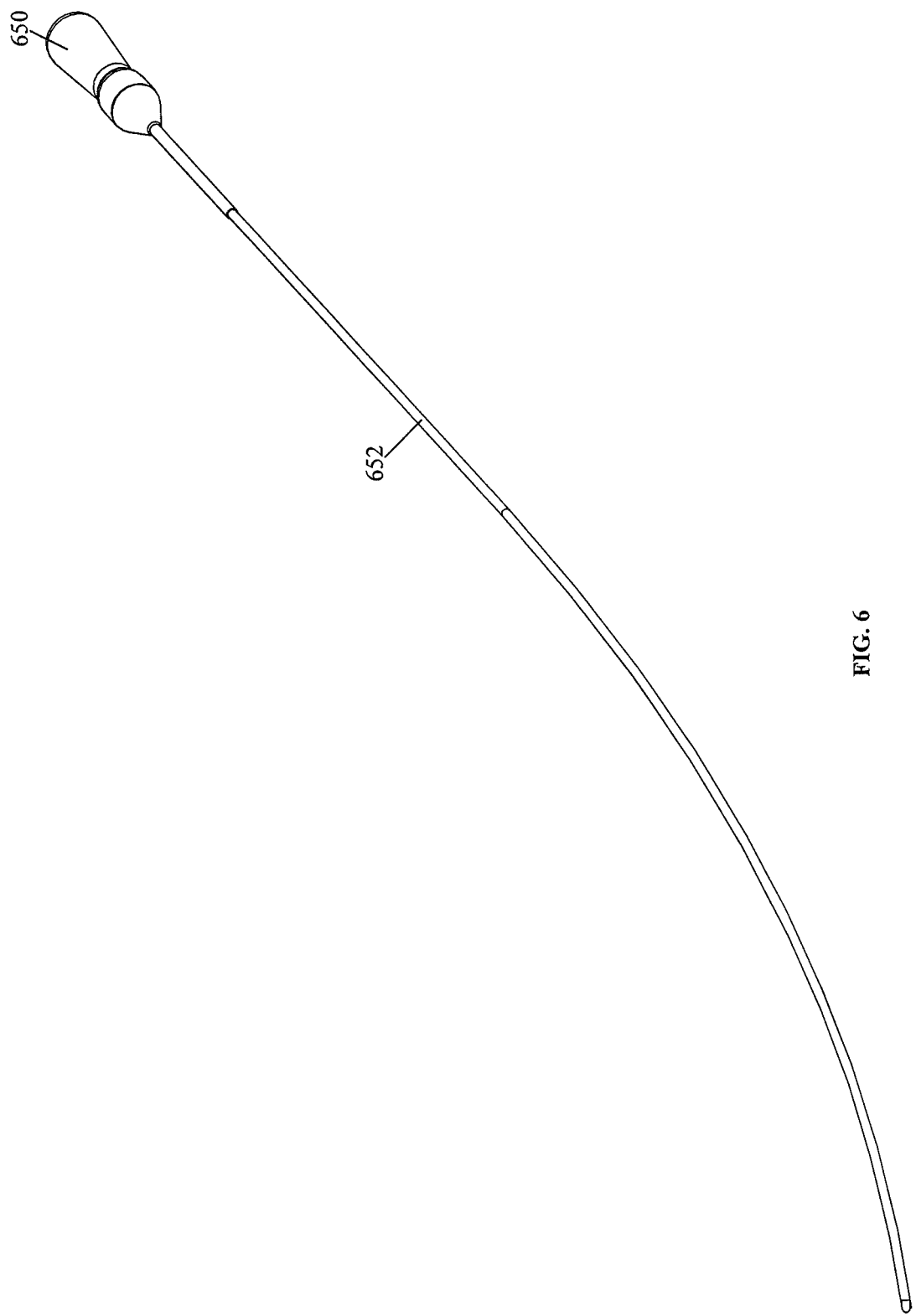
FIG. 6 shows a perspective view of an embodiment of a light pipe for use with a device for repairing a weakened or fractured bone of the presently disclosed embodiments.

FIG. 6 shows an embodiment of a light pipe 652 for use with a device for repairing a weakened or fractured bone of the presently disclosed embodiments. The light pipe 652 is connected to a light source (not shown) through a connector 650, and unlike the light pipe 452 depicted in FIG. 4, the light pipe 652 does not terminate in an optical lens. The light pipe 652 is connected to a light source (not shown) through a connector 650. Light emitted by the light pipe 652 is used to harden the reinforcing material that has been infused into a balloon portion of a delivery catheter of the device. Energy emitted from the light pipe 652 is guided into a balloon portion of a delivery catheter of a device of the presently disclosed embodiments.

The light pipe 652 is introduced into a side arm of an adapter that engages a proximal end of the delivery catheter of the device. The light pipe 652 runs through an elongated shaft of the delivery catheter of the device, through a light pipe conduit. In an embodiment, the light pipe 652 will be positioned within the light pipe conduit such that it is positioned within a separation area of the device. The separation area is located at a junction between a proximal end of the balloon portion and the elongated shaft. Activation of a light source, which connects to the light pipe 652 through the connector 650, communicates light down the light pipe 652 to cure the reinforcing material resulting in the affixing of the balloon portion in an expanded shape. A cure may refer to any chemical, physical, and/or mechanical transformation that allows a composition to progress from a form (e.g., flowable form) that allows it to be delivered through the void in the delivery catheter, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

Figure 7:
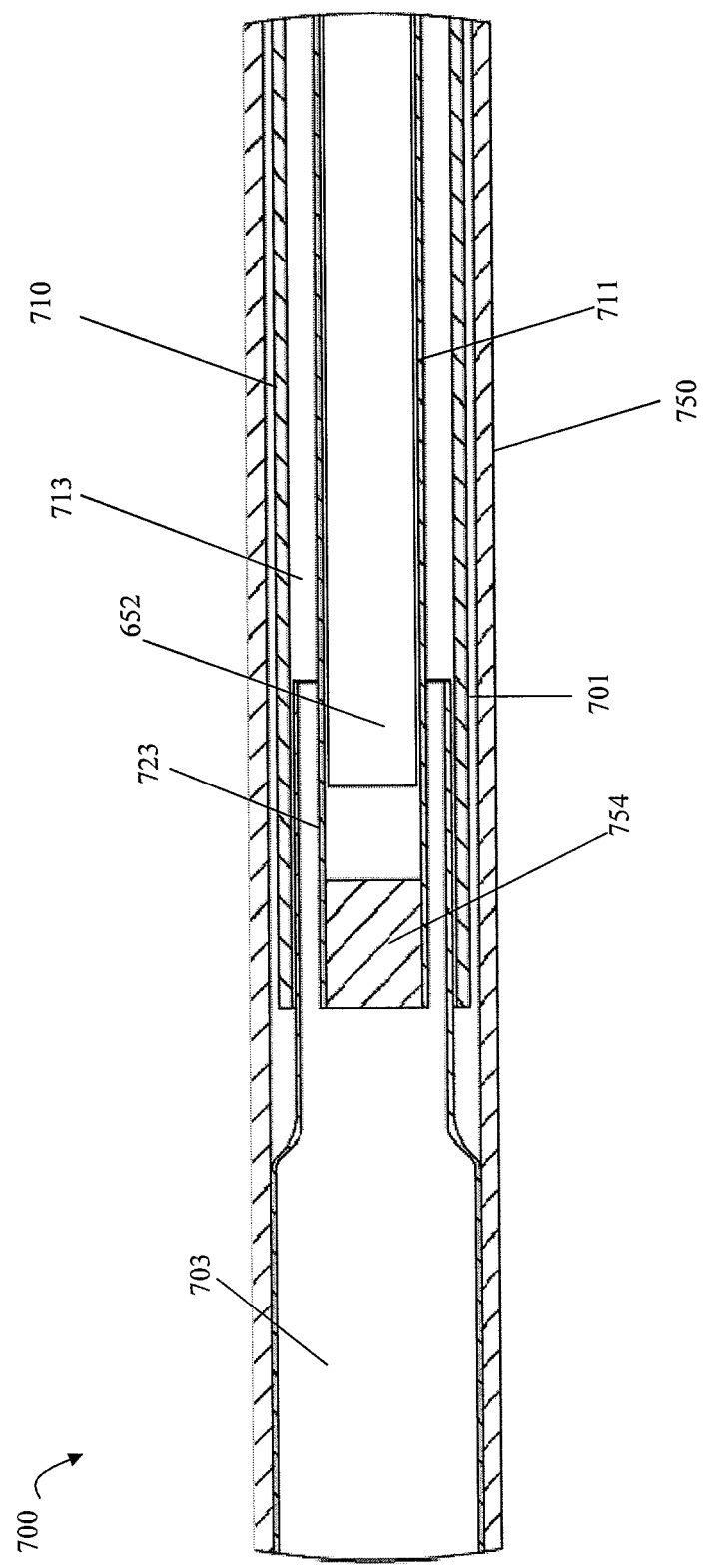
FIG. 7 shows a side cross-sectional view of an embodiment of a device having the light pipe of FIG. 6 for repairing a weakened or fractured bone of the presently disclosed embodiments.

In an embodiment, a device for repairing a fractured bone includes a delivery catheter having an elongated shaft with a proximal end, a distal end, and a longitudinal axis therebetween, the delivery catheter having an inner void for passing at least one reinforcing material, and an inner lumen for accepting a light pipe, wherein a distal end of the inner lumen terminates in an optical lens; a conformable member releasably engaging the distal end of the delivery catheter, the conformable member moving from a deflated state to an inflated state when the at least one reinforcing material is delivered to the conformable member; and an adapter releasably engaging the proximal end of the delivery catheter for receiving the light pipe and the at least one reinforcing material. FIG. 7 shows a side cross-sectional view of an embodiment of some of the main components of a device 700 for repairing a fractured bone. Device 700 includes a delivery catheter 710 having an elongated shaft 701 with a light pipe conduit 711. The light pipe conduit 711 accepts the light pipe 652 of FIG. 6. As shown in FIG. 7, the device 700 is positioned within a sheath 750. The light pipe 652 is used to communicate light energy towards a conformable member 703 of the device 700, and to harden reinforcing material that has been infused into the conformable member 703 of the device 700 via inner void 713. Energy emitted from the light pipe 652 is projected through an optical lens 754 that engages a distal end 723 of the light pipe conduit 711, and is guided into the conformable member 703. The optical lens 754 transmits light energy from the light pipe 652 to the conformable member 703. FIG. 7 shows the optical lens 754 at a distance away from the light pipe 652 for clarity. Typically during use however, the light pipe 652 abuts the optical lens 754. The optical lens 754 may be convex, concave or planar. The optical lens 754 can converge or diverge the transmitted light energy from the light pipe 652. The transmitted light energy hardens the reinforcing material within the conformable member 703.

In some embodiments, the intensity of light may be sufficient enough to reach the distal end of the conformable member (e.g., balloon portion) if the light pipe (e.g., optical fibers) is held in close proximity to or contacting/abutting the conformable member. By knowing the energy required to cure the reinforcing material or polymerize the monomer and calculating the distance from the light pipe to the most distal aspect of the conformable member, the inverse square law may be used to calculate how much energy will dissipate over the distance and therefore whether the light pipe can be abutted to the conformable member or need be placed within the conformable member so that it is closer to the reinforcing material. Not only is the distance from the light pipe to the reinforcing material reduced by placing the light pipe inside the conformable member, but the overall necessary intensity of light may be reduced.

In an embodiment, a device for use in repairing a fractured bone includes a delivery catheter having an elongated shaft with a proximal end, a distal end, and a longitudinal axis therebetween, the delivery catheter having an inner void for passing at least one reinforcing material, and an inner lumen for accepting an optical fiber; a conformable member releasably engaging the distal end of the delivery catheter, the conformable member having an inner lumen for accepting the optical fiber, the conformable member moving from a deflated state to an inflated state when the at least one reinforcing material is delivered to the conformable member; and an adapter releasably engaging the proximal end of the delivery catheter for receiving the optical fiber and the at least one reinforcing material.

Figure 8:
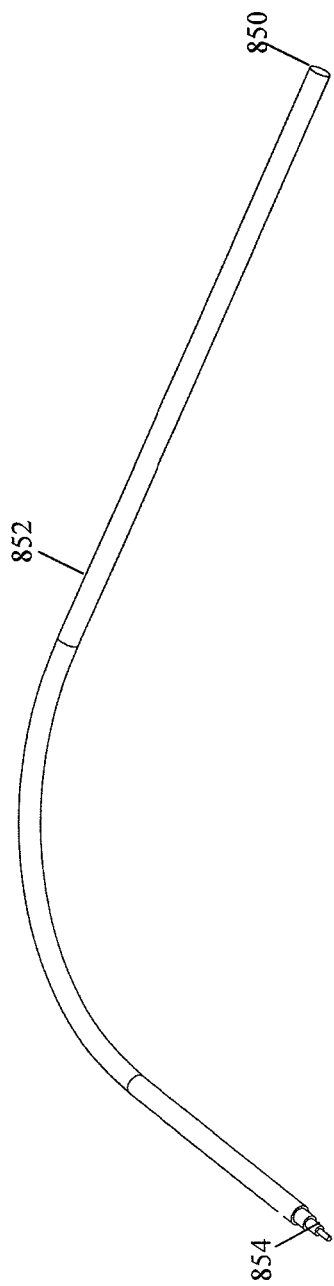
FIG. 8 shows a perspective view of an illustrative embodiment of an optical fiber for use with a device for repairing a weakened or fractured bone of the presently disclosed embodiments.
Figure 9E:
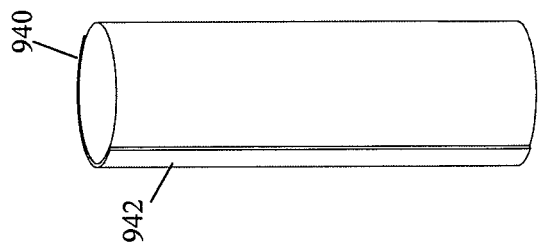
FIGS. 9A-9E show close-up perspective views of illustrative embodiments of modifications to a portion of an optical fiber of the presently disclosed embodiments.
Figure 9D:
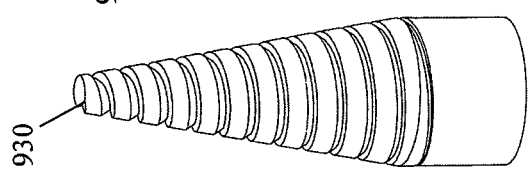
Figure 9C:
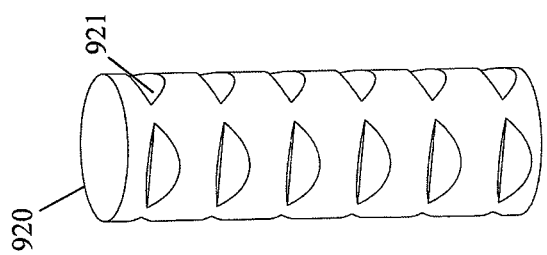
Figure 9B:
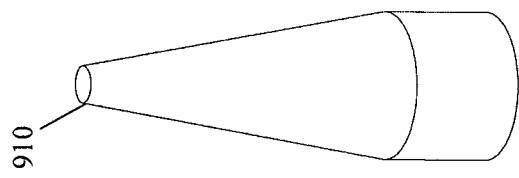
Figure 9A:
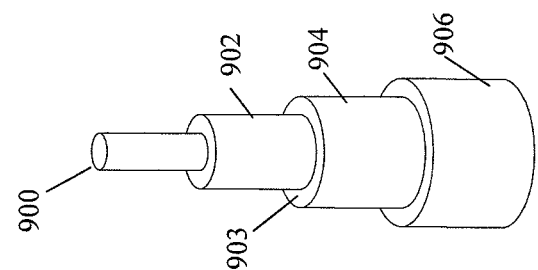

FIG. 8 shows a perspective view of an embodiment of a light pipe which is an optical fiber 852 for use with a device for repairing a weakened or fractured bone of the presently disclosed embodiments. In some embodiments, an optical fiber similar to the LUMENYTE STA-FLEX SEL end light Optical Fiber, available from Lumenyte International Corporation of Foothill Ranch, Calif., can be employed. These optical fibers may each consist of a light transmitting solid large core, a Teflon® clad and a black bondable outer jacket. The optical fiber 852 may transmit light from a light source to the output end 854 for use as a point source. The optical fiber 852 may have a wide 80 degree acceptance angle and 80 degree beam spread, allowing the light to be viewed from more oblique angles. The light transmitting core may be solid, may have no light diminishing packing fraction losses and may be easily spliced. The jacket may be bondable. Custom jackets may be available for more flexibility and color options.

The optical fiber 852 can each have a transmission loss (attenuation) of less than approximately 1.5% per foot, a bend radius (minimum) of approximately 6 times the fiber's 852 diameter, temperature stability of up to approximately 90° C. (194° F.), spectral transmission range of approximately 350-800 nm, an acceptance angle of approximately 80°, a refractive index core of approximately 1.48 or greater, cladding of approximately 1.34 or less and a numerical aperture of approximately 0.63. The length of the optical fiber 852 can be approximately 100 continuous feet. Splicing may be achieved in the field using a splice kit, such as the Lumenyte Splice Kit, and carefully following the instructions. Factory splicing may be an option. An optic cutter, such as Lumenyte's Optic Cutter, may be advised for straight, clean, 90° fiber cuts. These fibers may be installed by removing approximately 4 inches (10 cm) of the outer jacket (not the fluoropolymer cladding) before inserting fiber 852 into the light source. An end 850 of the fiber 852 may be near, but not touching the illuminator (light source) glass to assist in achieving maximum brightness. In some embodiments, the optical fiber 852 has some or all of the properties and/or characteristics exhibited by ESKA™ High-performance Plastic Optical Fiber: SK-10 and SK-60 and/or ESKA™ Plastic Fiber Optic & Cable Wiring, manufactured by Mitsubishi Rayon Co., Ltd., which are all available from Mitsubishi International Corporation of New York, N.Y. It should be appreciated that the above-described characteristics and properties of the optical fibers are exemplary and not all embodiments of the present invention are intended to be limited in these respects.

An optical fiber uses a construction of concentric layers for optical and mechanical advantages. The most basic function of a fiber is to guide light, i.e., to keep light concentrated over longer propagation distances—despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding is usually protected with at least a polymer coating. Light is kept in the "core" of the optical fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face. In some embodiments of the present disclosure, at least a portion of a length of an optical fiber is modified, e.g., by removing the cladding, in order to alter the direction, propagation, amount, intensity, angle of incidence, uniformity and/or distribution of light.

FIGS. 9A-9E show close-up perspective views of illustrative embodiments of modifications to a length of an optical fiber of the presently disclosed embodiments. In the embodiments shown in FIGS. 9A-9E, the optical fibers are modified in order to alter the direction, propagation, amount, intensity, angle of incidence, uniformity, dispersion and/or distribution of light. In an embodiment, the optical fiber is modified such that the light energy is dispersed along at least a portion of a length of the optical fiber. In an embodiment, the dispersion of light energy along the length of the optical fiber is achieved by modifying a surface of the optical fiber. In an embodiment, the dispersion of light energy from the optical fiber occurs in a radial direction. As shown in the embodiment depicted in FIG. 9A, circular steps (902, 904 and 906) may be created or cut into an optical fiber 900 of the present disclosure to cause the light to disperse along each terminating face 903 of each circular step (902, 904 and 906) of the optical fiber 900. In some embodiments, it may be desirable to remove some, all, or portions of the cladding of the optical fibers of the present disclosure. As shown in the embodiment in FIG. 9B, an optical fiber 910 has been tapered along a length, and some of the cladding has been removed. The tapering of the optical fiber 910 can result in a radial dispersion of light from the optical fiber 910. As shown in the embodiment depicted in FIG. 9C, notches 921 can be made into an optical fiber 920 to cause the internal reflectance to be directed outwards at an angle from the notch 921 in the fiber 920. In some embodiments, the notches may be created at about a 45 degree angle to the fiber. In some embodiments, the notches may be created at about a 30 degree angle, about a 62.5 degree angle or any angle less than about 45 degrees or greater than about 45 degrees as not all embodiments of the present invention are intended to be limited in this manner. Further, in some embodiments the angle of the notches may change depending on where the notch is located along the length of the fiber. For example, an optical fiber may be notched so that the angle of the notches which will be positioned at the ends of the balloon have a shallower angle than those to be positioned at middle of the balloon. In some embodiments, the ends of individual optical fibers that make up an optical fiber bundle may be staggered to enable light to emit from the light source at various locations along the length of the fiber. In some of the above described embodiments, the light need only travel a shorter distance to reach the glue, by allowing the light to travel widthwise, or radially, within the balloon. As shown in the embodiment depicted in FIG. 9D, a length of cladding of an optical fiber 930 has been modified by forming a helical design along a length of the optical fiber 930. As shown in the embodiment depicted in FIG. 9E, a portion of cladding 942 has been removed from optical fiber 940.

In some embodiments, optical elements may be oriented in alignment with the notches or openings in the optical fibers to adjust the light output. Such optical elements may include lenses, prisms, filters, spliters, diffusers and/or holographic films. The light source, and more specifically, the optical fibers may have some or all of the properties and features listed in U.S. Pat. No. 6,289,150, which is hereby incorporated by reference in its entirety, as not all embodiments of the present invention are intended to be limited in these respects.

In some embodiments, the optical fiber may include an optical fiber core surrounded by cladding and one or more illuminators. The illuminators may be of uniform size and shape positioned in a predetermined, spaced-apart relation, linearly, along a side of the optical fiber core. The optical fiber core may be received in a track and/or holder and/or reflector comprising a channel constructed with a reflective interior surface centered about the illuminators. The holder and/or reflector may be positioned adjacent to or in contact with the plurality of illuminators. A light source may be connected at one end of the optical fiber conduit in a conventional manner so as to cause a TIR effect. The end of the optical fiber conduit opposite the light source may include a reflective surface for reflecting back towards the light source any light remaining in the optical fiber conduit. For longer spans of optical conduit, the conduit may include a second light source.

The illuminators may include any non-uniformity, constructed into the optical fiber core during or after fabrication, that reflects or refracts light such as, for example bubbles, prisms, lenses or reflective material formed in the core during fabrication or after fabrication. Also, notches made from two cuts in the core to remove a wedge of material or singular cuts made in the core may function as the illuminators. Illuminators, such as notches or cuts may be made by using a mechanical cutter which may be capable of cutting the core uniformly and leaving a smooth, texture-free surface. A cutter suitable for this purpose may cut the core without tearing or burning the material. A cutter may have a circular disk shaped knife having a smooth, tooth-free blade that is freely rotatable about an axle located at the center of the disk. The blade may be angled at 45 degrees relative to the longitudinal axis of the core to cut a 90 degree notch wherein material having a crescent or triangular shape is removed from the core.

The notch may function as an illuminator by maximizing the TIR effect of light within the core. This may be due to the core having a different index of refraction from the ambient air in the notch which may direct the light across the core and out the opposite side of the core. Different lighting effects may be achieved by replacing the ambient air with other gases or compounds. Imperfections in the cut may direct some light into the notch. This light may reflects back through the core.

In some embodiments, where cuts are preferred over notches, the cut may be made at a uniform depth of ⅛ inch into the cladding and core and at a 45 degree angle from the horizontal, i.e., the longitudinal axis of the optical fiber. This may appear to cause the light to exit perpendicular to the longitudinal axis of the optical fiber where the optical fiber core may have an acceptance angle of approximately 81 degrees to allow light to exit. The surface of the sides of the cut may be smooth rather than rough to ensure light is refracted uniformly. The cut may form a wedge which has a gap sufficient to prevent contact between the sides of the cut during normal use. Such contact may reduce the light reflecting and/or refracting properties. In some embodiments, the cuts may be less efficient than the notches in relying on TIR to force light out of core. A holder which may fix the optical fibers in desired alignment may also act as a holder and/or reflector. In some embodiments, when the optical fiber may be round in cross section and may be placed in a nonconforming holder such as a rectilinear "U" channel where an open space is created at the bottom of the "U", cuts may be made in the optical fibers that come in close proximity to the bottom of the "U" to maintain this configuration. In some embodiments where a conforming holder may be used, the cuts may close and alter the configuration such that efficiency of light extraction may be reduced. In some embodiments when using a conforming holder, illuminators may be made with notches sufficient to maintain an open space between the holder and notched surface.

In some embodiments, cutting notches may include using a high speed drill motor with a cutting blade sufficient to make a notch in the optical fiber such that the surface created with the notch may be smooth enough to allow total internal reflection to occur. Alignment of illuminator or illuminators with respect to the holder may determine the directionality of the light output emitted from the optical system. The shape of the cut may effect the output beam pattern of the optical system. For example, the wider the cut, the wider the output beam pattern As with most linear fiber optics, as light is extracted from lengths of the fiber near the light source there may be less light available in subsequent lengths and this occurrence may be taken into consideration in the manufacturing process. In some embodiments, to achieve uniform lighting from the optical fiber conduit, the frequency with which the illuminators occur may increase non-linearly in relation to the length of the conduit and the distance of the illuminators from the light source. In other words, the illuminators may be closer together as the distance from the light source increases. This may compensate for the attenuation of the light due to the loss experienced from the illuminators and the natural attenuation of the optic itself. The spacing may be made progressively closer or in groups of spacing in which the groups may progressively get closer but the distance between individual illuminators within each group may remain constant. In some embodiments, the illuminators may have progressive depths to make the optical fibers transmit light evenly along its length. When illuminators are made progressively deeper, the light pattern may be altered. The deeper the cuts, the wider the light pattern may become. When illuminators are made progressively closer, the light pattern may remain the same and the light output may be increased. In some embodiments, near uniformity of light output along the length of the conduit may be achieved in part due to the changes in the spacing of the illuminators and in part due to the uniformity of the size and angle of the illuminators. A mechanical cutter may be well adapted to provide such uniformity.

While some embodiments may include continuous variations in the frequency of the cut spacing, the cutter may be adaptable to vary the frequency of the spacing at discrete intervals to minimize delays during adjustment of the spacing interval.

The illuminators may be made in optical fiber core alone before the cladding is added and/or the illuminators may be made in the cladding and the core after it has been surrounded by the cladding. In some embodiments, when the cladding is heated to tightly shrink around the core, the cladding may affect the uniformity of the illuminators in the core by either entering the notch or closing the cut thereby reducing the potential light deflecting properties of the illuminator.

The illuminators may be positioned to direct light across the greater diameter of an elliptical optical fiber core out and out through a region opposite from each of the respective illuminators. This may be accomplished by angling the notches and/or cuts to direct light from the light source through the optic core. The illuminators allow better control of escaping light by making the notches, which are positioned on one side of the optic to direct the light rather than allowing the cuts to reflect/refract light in various directions which reduces the contribution of light to a desired focusing effect.

One or more optical elements, such as diffusers, polarizers, magnifying lenses, prisms, holograms or any other element capable of modifying the direction, quantity or quality of the illumination, individually or in combination can also be added and aligned with the core-clad, notches and track or holder and/or reflector. The optical elements may be formed as separate components or formed integrally with the core, cladding and/or a jacketing material or in any combination of separate and integrally formed components. Optical elements formed integrally in the core and cladding of various shapes may create a lens and thereby affects the directionality of light from the finished product. Different optical fiber shapes may create different output beam patterns. In some embodiments, a round fiber optic may create a wider beam spread of light. In some embodiments, a wedge shaped optic may produce a collimated light beam spread. This beam spread may be due to what is believed to be a lensing effect. In some embodiments, the depth of the cut may at least intersect the focal point of the lens formed by the curvature of the optical fiber core where the light exits the core.

The optical fiber core may have any shape and the shape of the core may effect the diffusion of light. In some embodiments, the optical fiber core may be cylindrically shaped when viewed in cross-section and may form a lens that diffuses the light over a wide field of illumination. In some embodiments, the optical fiber core may have an oval or elliptical shape when viewed in cross-section and may form a lens that increases the intensity of the light within a narrower field of illumination. In some embodiments, the optical fiber core may have a wedge shape when viewed in a cross-section and may forms a lens. It will be appreciated that other shapes may be used because of their desired optical characteristics to also act as optical elements, as not all embodiments of the present invention are intended to be limited in this respect.

Alternative optical elements may also assist in achieving various lighting effects by including a separate optical element in alignment with the holder and/or reflector and the arc formed by the notch on the opposite side of the optic from the optical element. The lens optic, notch and holder and/or reflector may be aligned to direct light out of the optic and into the lens. The optical element may also be formed integrally in the jacketing material. The jacket thickness may be adjusted to achieve a desired lighting effect. Alternatively, cylindrically shaped diffusers may be included and aligned to generate other desired lighting effects. In some embodiments, a first diffuser may lower the intensity of light passing through an optical fiber and a second diffuser may increase the intensity of light passing through it. The two diffusers as thus described, may modify the intensity of light as it transmits and diverges away from the optical fiber.

In order to best make use of this kind of application specific optical lighting, it may be advisable to control the alignment of the illuminators, holder and/or reflectors and optical elements. In some embodiments, the alignment of these elements may be centered about a diameter of the fiber optic core (e.g., the diameter from and perpendicular to the center of the holder and/or reflector). It may be desirable to maintain control of this alignment along the entire length of the optical fiber conduit.

In an embodiment, a fracture repair process reinforces a weakened or fractured bone without exposing the bone through a traditional surgical incision. The presently disclosed embodiments use a minimally invasive approach by making a minor incision to gain access to the bone. Minimally invasive refers to surgical means, such as microsurgical, endoscopic or arthroscopic surgical means, that can be accomplished with minimal disruption of the pertinent musculature, for instance, without the need for open access to the tissue injury site or through minimal incisions. Minimally invasive procedures are often accomplished by the use of visualization such as fiber optic or microscopic visualization, and provide a post-operative recovery time that is substantially less than the recovery time that accompanies the corresponding open surgical approach. Benefits of minimally invasive procedures include causing less trauma because there is minimal blood loss, a reduction in surgery and anesthetized time, shortened hospitalization, and an easier and more rapid recovery. In an embodiment, a bone fixator may be placed within an intramedullary cavity of a weakened or fractured bone. By restoring and preserving bone structure, some of the presently disclosed embodiments permit additional future treatment options.

Figure 10A:
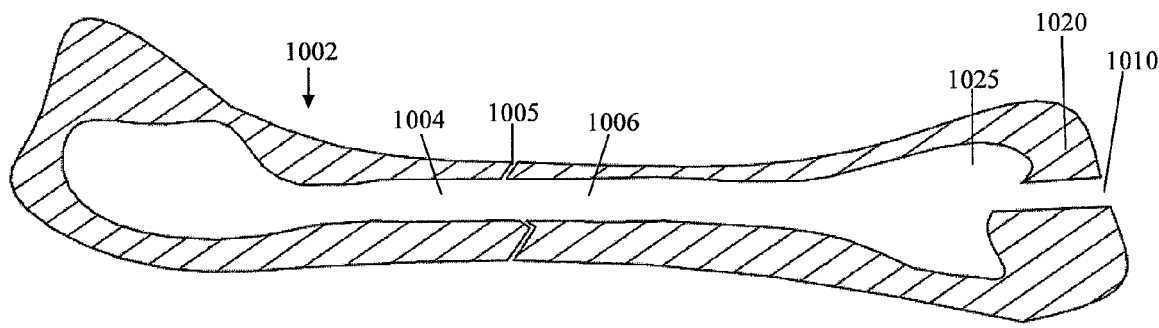
FIGS. 10A-10E show the method steps for utilizing a device of the presently disclosed embodiments for repair of a fractured bone.

FIGS. 10A-10E in conjunction with FIG. 1, illustrate an embodiment of the method steps for repairing a fractured bone in a patient's body. A minimally invasive incision (not shown) is made through the skin of the patient's body to expose a fractured bone 1002. The incision may be made at the proximal end or the distal end of the fractured bone 1002 to expose the bone surface. Once the bone 1002 is exposed, it may be necessary to retract some muscles and tissues that may be in view of the bone 1002. As shown in FIG. 10A, an access hole 1010 is formed in the bone by drilling or other methods known in the art. In an embodiment, the access hole 1010 has a diameter of about 3 mm to about 10 mm. In an embodiment, the access hole 1010 has a diameter of about 3 mm.

The access hole 1010 extends through a hard compact outer layer 1020 of the bone into the relatively porous inner or cancellous tissue 1025. For bones with marrow, the medullary material should be cleared from the medullary cavity prior to insertion of the device 100. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

Figure 10B:
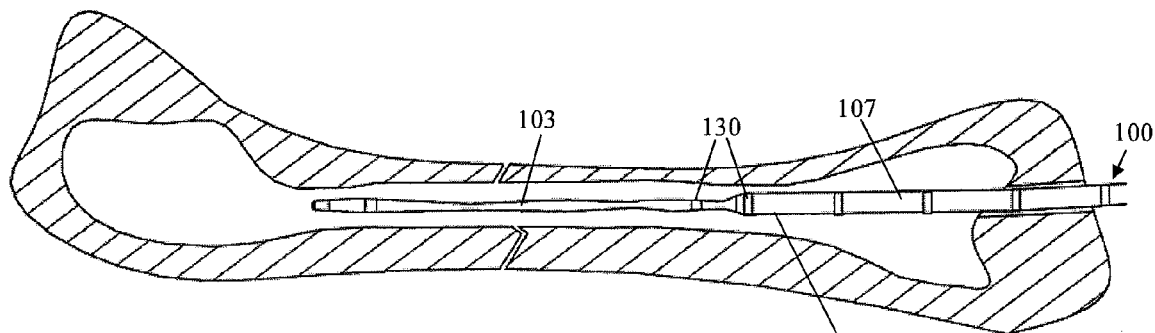
Figure 10C:
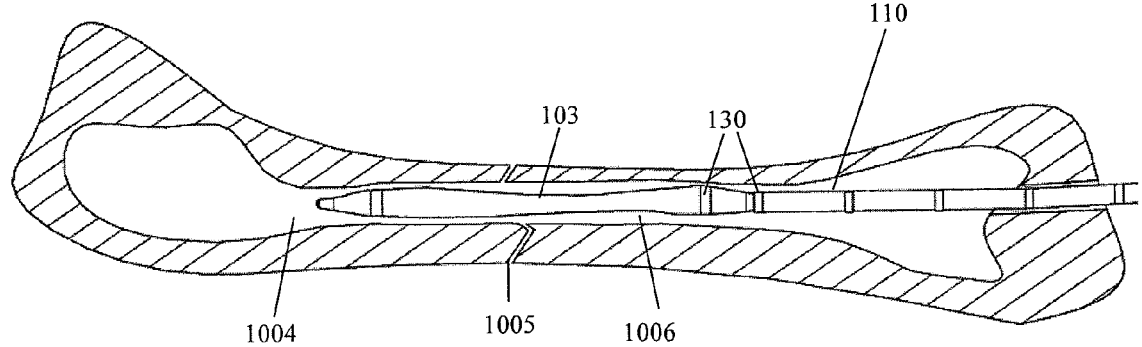

A guidewire (not shown) may be introduced into the bone 1002 via the access hole 1010 and placed between bone fragments 1004 and 1006 of the bone 1002 to cross the location of a fracture 1005. The guidewire may be delivered into the lumen of the bone 1002 and crosses the location of the break 1005 so that the guidewire spans multiple sections of bone fragments. As shown in FIG. 10B, the balloon portion 103 of the device 100 for repairing a fractured bone, which is constructed and arranged to accommodate the guidewire, is delivered over the guidewire to the site of the fracture 1005 and spans the bone fragments 1004 and 1006 of the bone 1002. Once the balloon portion 103 is in place, the guidewire may be removed. The location of the balloon portion 103 may be determined using at least one radiopaque marker 130 which is detectable from the outside or the inside of the bone 1002. For example, as shown in the embodiment depicted in FIG. 10, radiopaque markers 130, which are visible from outside of the body using x-ray or other detection means, are located along both the balloon portion 103 and the slip sleeve 107 of the delivery catheter 110 to help align and position the device 100. Once the balloon portion 103 is in the correct position within the fractured bone 1002, the device 100 is attached to a delivery system which contains a reinforcing material. The reinforcing material is then infused through a void in the delivery catheter 110 and enters the balloon portion 103 of the device 100. This addition of the reinforcing material within the balloon portion 103 causes the balloon portion 103 to expand, as shown in FIG. 10C. As the balloon portion 103 is expanded, the fracture 1005 is reduced. In an embodiment, the reinforcing material is a UV curable glue which requires a UV light source to cure the adhesive. In an embodiment, the reinforcing material requires a visible light source to cure the adhesive. In an embodiment, a central space may remain in the balloon portion 103 which may be filled in order to provide extra strength and support to the fractured bone 1002. An optical rod or similar device may be positioned in the central space and turned on or illuminated. An optical rod or similar device can be made of fiber, silica, quartz, sapphire or similar materials. The UV light will then harden the UV curable glue in the balloon portion 103. The end of the optical rod may be cut and remain in the balloon portion 103 to provide increased rigidity.

Figure 10D:
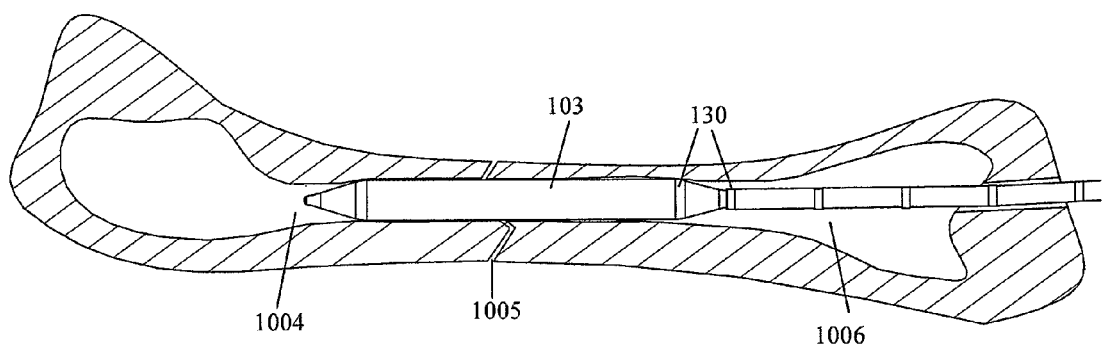
Figure 10E:
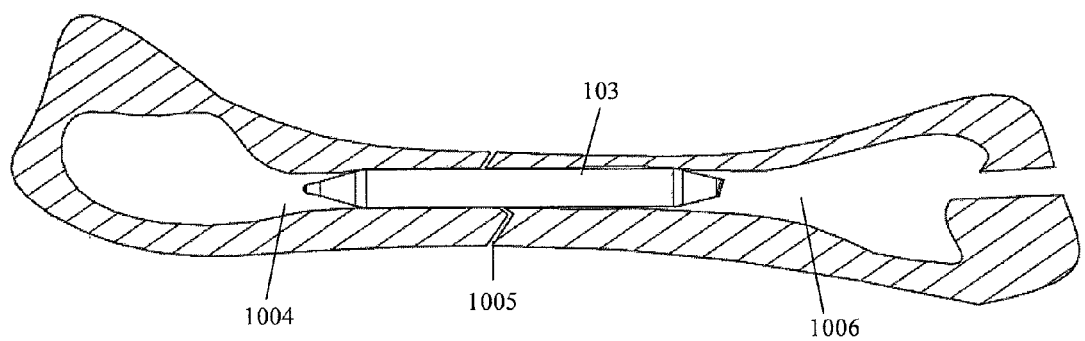

Once orientation of the bone fragments 1004 and 1006 are confirmed to be in a desired position, the UV curable glue may be hardened within the balloon portion 103, as shown in FIG. 10D, such as by illumination with a UV or visible emitting light source. After the UV curable glue has been hardened, the light pipe may be removed from the device 100. The balloon portion 103 once hardened, may be released from the delivery catheter 110 by known methods in the art. In an embodiment, the delivery catheter 110 is cut to separate the balloon portion 103 from the elongated shaft 101. A device slides over the delivery catheter 110 and allows a right angle scissor to descend through the delivery catheter 110 and make a cut. The location of the cut may be determined by using a fluoroscope or an x-ray. In an embodiment, the cut location is at the junction where the elongated shaft 101 meets the balloon portion 103.

In an embodiment, the device 100 is used to treat a hand or wrist fracture. The wrist is a collection of many joints and bones that allow use of the hands. The wrist has to be mobile while providing the strength for gripping. The wrist is complicated because every small bone forms a joint with its neighbor. The wrist comprises at least eight separate small bones called the carpal bones, that connect the two bones of the forearm, called the radius and the ulna, to the bones of the hand and fingers. The wrist may be injured in numerous ways. Some injuries seem to be no more than a simple sprain of the wrist when the injury occurs, but problems can develop years later. A hand fracture may occur when one of the small bones of the hand breaks. The hand consists of about 38 bones and any one of these bones may suffer a break. The palm or midhand is made up of the metacarpal bones. The metacarpal bones have muscular attachments and bridge the wrist to the individual fingers. These bones frequently are injured with direct trauma such as a crush from an object or most commonly the sudden stop of the hand by a wall. The joints are covered with articular cartilage that cushions the joints. Those skilled in the art will recognize that the disclosed device and methods can be used for to treat fractures to other bones, such as radius, ulna, clavicle, metacarpals, phalanx, metatarsals, phalanges, tibia, fibula, humerus, spine, ribs, vertebrae, and other bones and still be within the scope and spirit of the disclosed embodiments.

The presently disclosed embodiments may be used to treat a clavicle fracture, resulting in a clavicle reduction. The clavicle or collar bone is classified as a long bone that makes up part of the shoulder girdle (pectoral girdle). Present methods to affix a broken clavicle are limited. The clavicle is located just below the surface of the skin, so the potential for external fixation including plates and screws is limited. In addition, the lung and the subclavian artery reside below the collar bone so using screws is not an attractive option. Traditional treatment of clavicle fractures is to align the broken bone by putting it in place, provide a sling for the arm and shoulder and pain relief, and to allow the bone to heal itself, monitoring progress with X-rays every week or few weeks. There is no fixation, and the bone segments rejoin as callous formation and bone growth bring the fractured bone segments together. During healing there is much motion at the fracture union because there is not solid union and the callous formation often forms a discontinuity at the fracture site. A discontinuity in the collar bone shape often results from a clavicle fracture.

The presently disclosed embodiments and methods treat a clavicle fracture in a minimally invasive manner and may be used for a clavicle reduction or collar bone reduction. A benefit of using the disclosed device to repair a collar bone is the repair minimizes post repair misalignment of collar bone. A benefit of using the disclosed device to repair a clavicle is to resolve the patient's pain during the healing process.

Figure 11A:
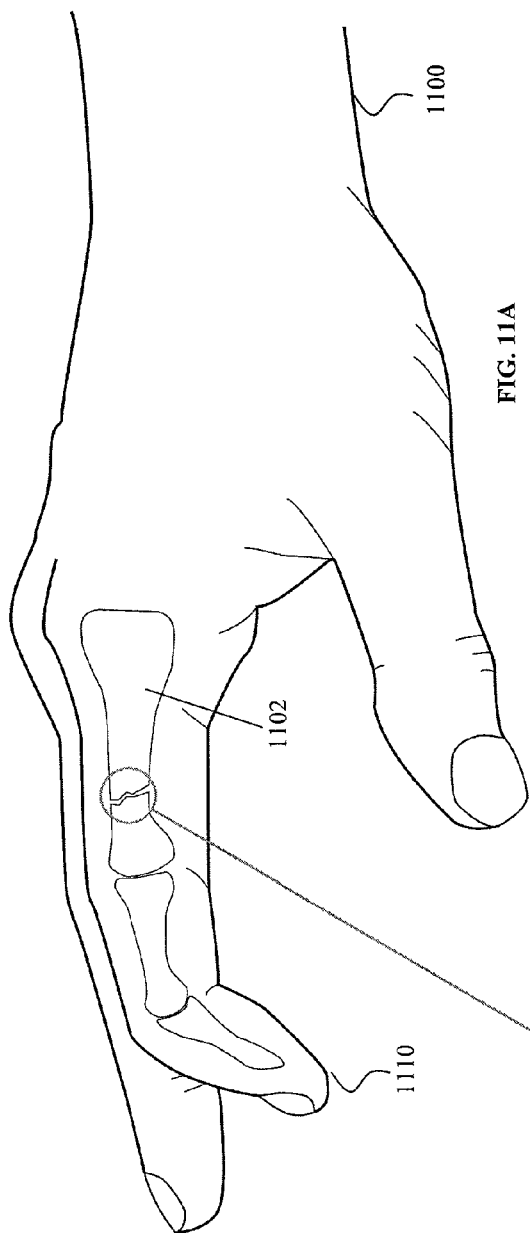
FIGS. 11A-11C show illustrative embodiments of a fractured metacarpal bone in a finger of a hand.
Figure 11C:
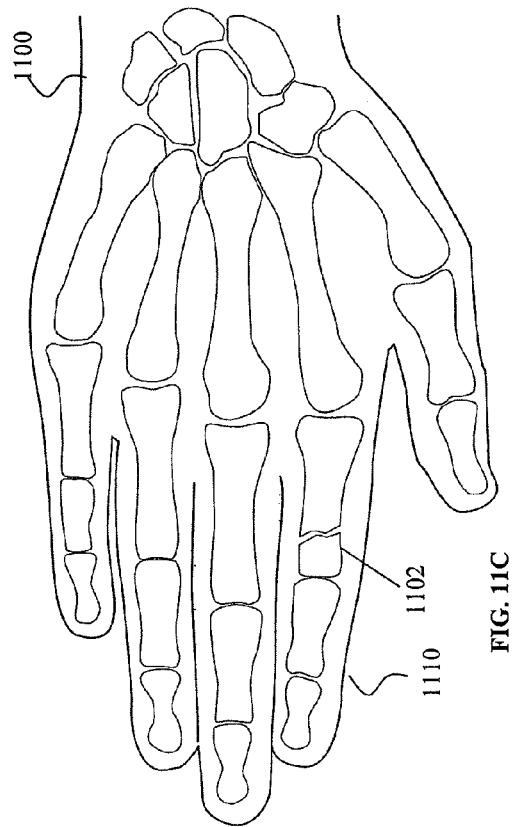
Figure 11B:
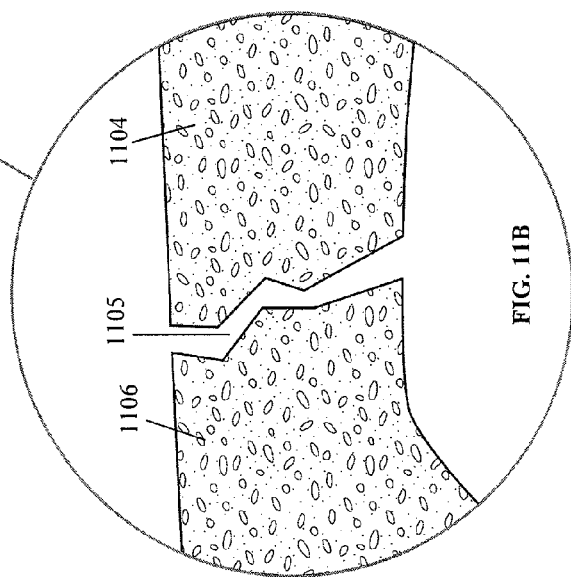

FIGS. 11A, 11B and 11C, in conjunction with FIGS. 12A, 12B and 12C, show a device 100 of the presently disclosed embodiments for use in repairing a fractured metacarpal bone 1102 in a finger 1110 in a hand 1100 of a patient. As shown, the fractured metacarpal bone 1102 has been split into two fragments, 1104 and 1106, at a break site 1105. As shown in FIG. 12A, the balloon portion of the device 100 is delivered to the site of the fracture 1105 and spans the bone fragments 1104 and 1106 of the bone 1102. The location of the balloon portion may be determined using at least one radiopaque marker which is detectable from the outside or the inside of the bone 1102. Once the balloon portion is in the correct position within the fractured bone 1102, the device 100 is attached to a delivery system which contains a reinforcing material. The reinforcing material is then infused through a void in the delivery catheter and enters the balloon portion of the device 100. This addition of the reinforcing material within the balloon portion causes the balloon portion to expand, as shown in FIG. 12B. As the balloon portion is expanded, the fracture 1105 is reduced. In an embodiment, the reinforcing material is a UV curable glue which requires a UV light source to cure the adhesive. The UV light will then harden the UV curable glue in the balloon portion. In an embodiment, the reinforcing material requires a visible light source to cure the adhesive.

Once orientation of the bone fragments 1104 and 1106 are confirmed to be in a desired position, the UV curable glue may be hardened within the balloon portion, such as by illumination with a UV emitting light source. After the UV curable glue has been hardened, the light pipe may be removed from the device 100. The balloon portion once hardened, may be released from the delivery catheter by known methods in the art, as shown in FIG. 12C. In an embodiment, the delivery catheter is cut to separate the balloon portion from the elongated shaft.

A method for repairing a fractured bone includes gaining access to an inner cavity of the fractured bone; providing a device for use in repairing the fractured bone, the device comprising a delivery catheter having an inner void for passing at least one reinforcing material and an inner lumen for accepting an optical fiber, the delivery catheter releasably engaging a conformable member having an inner lumen for passing the optical fiber; positioning the conformable member spanning at least two bone segments of the fractured bone; inserting the optical fiber into the inner lumen of the conformable member; introducing the at least one reinforcing material through the inner void of the delivery catheter for infusing the reinforcing material within the conformable member, wherein the conformable member moves from a deflated state to an inflated state; activating a light source that is connected to the optical fiber to communicate light energy into the inner lumen of the conformable member such that the at least one reinforcing material is hardened; and releasing the hardened conformable member from the delivery catheter.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An internal bone fixation device comprising:
   a delivery catheter having an elongated shaft with a proximal end, a distal end, and a longitudinal axis therebetween, the delivery catheter having an inner void for passing at least one reinforcing material, and an inner lumen;
   a balloon portion extending from the distal end of the delivery catheter, wherein the balloon portion is expandable from a deflated state to an inflated state by adding the at least one reinforcing material into the balloon portion; and
   an optical fiber sized to pass through the inner lumen of the delivery catheter and into the balloon portion, wherein a core of the optical fiber is modified such that, when the optical fiber is in the balloon portion, the optical fiber is able to disperse the light energy along at least a portion of the length of the optical fiber to cure the at least one reinforcing material within the balloon portion.

2. The device of claim 1 further comprising a cladding surrounding the core of the optical fiber.

3. The device of claim 2 wherein the core of the optical fiber is exposed by removing a portion of the cladding.

4. The device of claim 2 wherein a distal portion of the optical fiber is modified by cutting at least one notch into the cladding to expose the core of the optical fiber.

5. The device of claim 1 wherein a distal portion of the optical fiber is modified by removing varying amounts of a cladding along the distal portion to create one or more terminating faces to disperse the light energy.

6. The device of claim 1 wherein a distal portion of the optical fiber is modified by removing a cladding from the optical fiber to create a helical design on a surface of the optical fiber to disperse the light energy along the length and at a distal end of the optical fiber in a helical pattern.

7. The device of claim 1 further comprising an adapter releasably engaging the proximal end of the delivery catheter for receiving the optical fiber and the at least one reinforcing material.

8. The device of claim 1 further comprising an optical lens that transmits the light energy from the optical fiber to the balloon portion.

9. The device of claim 1 further comprising one or more illuminators within the core of the optical fiber.

10. The device of claim 1 further comprising a light source for providing the light energy to the optical fiber.

11. An internal bone fixation device comprising:
a delivery catheter having an elongated shaft with a proximal end, a distal end, and a longitudinal axis therebetween, the delivery catheter having an inner void for passage of at least one reinforcing material, and an inner lumen;
a balloon portion extending from the distal end of the delivery catheter, the balloon portion expandable from a deflated state to an inflated state by passing the at least one reinforcing material into the balloon portion; and
an optical fiber sized to pass through the inner lumen of the delivery catheter and into the balloon portion, wherein, when the optical fiber is in the balloon portion, the optical fiber disperses the light energy in a radial direction to cure the at least one reinforcing material within the balloon portion.

12. The device of claim 11 wherein the optical fiber disperses the light energy along a length of the optical fiber.

13. The device of claim 11 wherein the optical fiber includes a core surrounded by a cladding.

14. The device of claim 13 wherein the output end is tapered by removing a portion of the cladding surrounding the core along a length of the optical fiber.

15. The device of claim 11 further comprising one or more illuminators within a core of the optical fiber.

16. The device of claim 11 further comprising an optical lens that transmits the light energy from the optical fiber to the balloon portion.

17. The device of claim 11 further comprising a light source for providing the light energy to the optical fiber.

18. A kit for repairing a weakened or fractured bone, the kit comprising:
an optical fiber, wherein at least a distal portion of the optical fiber is modified, and wherein the distal portion of the optical fiber is configured to disperse light energy at along at least a portion of a length of the distal portion of the optical fiber;
at least one reinforcing material; and
a delivery catheter having an elongated shaft with a proximal end, a distal end, and a longitudinal axis therebetween, wherein the delivery catheter has an inner void for passing the at least one reinforcing material into a balloon portion extending from the distal end of the delivery catheter, and wherein the delivery catheter has an inner lumen for passing the optical fiber into the balloon portion.

19. The kit of claim 18 further comprising an adapter to be releasably engaged to the proximal end of the delivery catheter for receiving the optical fiber and the at least one reinforcing material.

20. The kit of claim 18 further comprising a light source for providing the light energy to the optical fiber.

* * * * *